(12) United States Patent
Robert et al.

(10) Patent No.: US 9,987,098 B2
(45) Date of Patent: Jun. 5, 2018

(54) APPARATUS FOR CLEANING MEDICAL INSTRUMENTS

(71) Applicant: STERIS INC., Temecula, CA (US)

(72) Inventors: Maxime Robert, L'Ancienne Lorette (CA); Louis Martineau, St-Nicolas (CA)

(73) Assignee: STERIS INC., Temecula, CA (US)

( * ) Notice: Subject to any disclaimer, the term of this patent is extended or adjusted under 35 U.S.C. 154(b) by 164 days.

(21) Appl. No.: 15/040,298

(22) Filed: Feb. 10, 2016

(65) Prior Publication Data

US 2016/0242868 A1 Aug. 25, 2016

Related U.S. Application Data

(60) Provisional application No. 62/278,086, filed on Jan. 13, 2016, provisional application No. 62/118,601, filed on Feb. 20, 2015.

(51) Int. Cl.
*A47L 15/50* (2006.01)
*A61B 90/70* (2016.01)
*A61B 50/22* (2016.01)

(52) U.S. Cl.
CPC ............ *A61B 90/70* (2016.02); *A47L 15/508* (2013.01); *A61B 50/22* (2016.02)

(58) Field of Classification Search
CPC ......... A61L 2/26; A61B 90/70; A61B 90/701; A61B 50/20; A61B 50/21; A61B 50/22; A61B 50/24; A47L 15/50; A47L 15/505; A47L 15/508; A47L 15/4202; A47L 15/4204; A47L 15/4206; A47L 15/4208; B08B 9/20; B08B 9/28; B08B 9/42; B08B 9/423; B08B 9/426
See application file for complete search history.

(56) References Cited

U.S. PATENT DOCUMENTS

| 5,749,385 A | 5/1998 | Rochette et al. ............. 134/199 |
| 6,675,977 B2 * | 1/2004 | Parks .................... A47L 15/505 211/41.8 |
| 2002/0001537 A1 | 1/2002 | Hlebovy et al. ................ 422/28 |

(Continued)

FOREIGN PATENT DOCUMENTS

| DE | 102008011743 A1 | 9/2009 | ............... A61L 2/26 |
| WO | WO 2005/011513 A1 | 2/2005 | ............. A61B 19/02 |

OTHER PUBLICATIONS

Machine Translation of Simmoteit, DE 102008011743, Sep. 2009.*

(Continued)

*Primary Examiner* — David G Cormier
(74) *Attorney, Agent, or Firm* — Kusner & Jaffe; Michael A. Centanni

(57) ABSTRACT

A rack for holding and washing surgical instruments in a washer/disinfector includes a frame assembly having tubular sections, a rotary spray arm mounted to the frame assembly, a fluid inlet positioned on the frame assembly to connect the frame assembly to the washer/disinfector, a first fluid path defined from the fluid inlet to the spray nozzles through one or more of the tubular sections to direct fluid from the washer/disinfector to the spray nozzles, a second fluid path defined from the fluid inlet to connectors through the tubular section, a filter for fluids from the fluid inlet, and a securing system to secure the surgical instruments.

11 Claims, 18 Drawing Sheets

(56) References Cited

U.S. PATENT DOCUMENTS

| | | | |
|---|---|---|---|
| 2007/0207074 A1 | 9/2007 | Jethrow | 422/292 |
| 2009/0286030 A1* | 11/2009 | Robert | A61L 2/18 |
| | | | 428/36.91 |
| 2013/0306112 A1 | 11/2013 | Blumenkranz | 134/34 |
| 2016/0193012 A1 | 7/2016 | Anderson et al. | A61B 90/70 |

OTHER PUBLICATIONS

International Search Report issued in corresponding International Patent Application No. PCT/US2016/018633, dated May 6, 2016.

* cited by examiner

APPARATUS FOR CLEANING MEDICAL INSTRUMENTS

RELATED APPLICATIONS

This application claims the benefit of U.S. Provisional Application No. 62/118,601, filed Feb. 20, 2015, and U.S. Provisional Application No. 62/278,086, filed Jan. 13, 2016, which are hereby fully incorporated herein by reference.

FIELD OF THE INVENTION

The present invention relates generally to the art of cleaning and decontamination and, more particularly, to an apparatus for cleaning, washing, sterilizing, and disinfecting complex, intricate surgical instruments, such as, "wristed" surgical instruments used on robotic surgical platforms.

BACKGROUND OF THE INVENTION

In recent years, the use of sophisticated robotic platforms for surgical procedures has increased. These robotic platforms employ small, intricate, "wristed" surgical instruments that are controlled by a surgeon. When in use during a surgical procedure, the ends of these intricate surgical components are inserted into a patient through small incisions in a patient's body. Therefore, washing and disinfection of the robotic instruments are necessary following each surgical use.

SUMMARY OF THE INVENTION

Example embodiments of the present invention provide an apparatus for automated washing and disinfection of robotic surgical instruments.

In one aspect of the example embodiments, a rack for holding and washing surgical instruments in a washer/disinfector includes a frame assembly having a plurality of tubular sections. The frame assembly defines an interior region configured to receive the surgical instruments for respective positioning therein. A rotary spray arm of the rack is mounted to the frame assembly. The spray arm has a plurality of spray nozzles configured to direct a fluid provided from the tubular sections toward the surgical instruments respectively positioned within the interior region. A fluid inlet of the rack is positioned on the frame assembly. The fluid inlet is configured to connect to the frame assembly to a fluid circulation system in the washer/disinfector. The fluid inlet is further configured to provide the fluid to the tubular sections from the fluid circulation system. A first fluid path of the rack is defined from the fluid inlet to the spray nozzles through the tubular sections. The first fluid path is configured to direct the fluid from the fluid inlet to the spray nozzles. A second fluid path of the rack is defined from the fluid inlet to a plurality of connectors through the tubular section. The second fluid path is configured to direct the fluid from the fluid inlet to the connectors. Each of the connectors is configured to connect to a respective one of the surgical instruments and provide the fluid thereto. A filter of the rack is configured to filter the fluid from the fluid inlet. A securing system of the rack is configured to secure each of the surgical instruments in a predetermined orientation in the interior region that is consistent with a configuration of the surgical instruments. The securing system includes a support bracket configured to secure each of the connectors for connection to the respective one of the surgical instruments to provide the fluid thereto.

In another example of the first aspect, the filter defines the first and second fluid paths. In another example of the first aspect, the filter includes a housing having a removable filter cartridge disposed therein. In yet another example of the first aspect, the filter is positioned between the fluid inlet and the first and second fluid paths.

The support bracket in an example of the first aspect includes a plurality of bracket positions. The bracket positions each are configured to secure one of the connectors for connection to the respective one of the surgical instruments to provide fluid thereto. Each of the connectors in an example of the first aspect is one of a plurality of types of connectors. Each of the connector types is configured to connect to a corresponding type of the surgical instruments to provide fluid thereto.

The securing system in an example of the first aspect includes a plurality of polymeric restraints coupled to the support bracket. Each of the polymeric restraints is configured to force the respective one of the surgical instruments toward the support bracket to secure the respective one of the surgical instruments to the support bracket. Each of the polymeric restraints may include a body portion and a pair of end portions oppositely extending from the body. Each of the end portions of the polymeric restraints may be configured to attach to the support bracket. A plurality of apertures may be formed in the support bracket. Each of the end portions of the polymeric restraint may be positioned and secured within the apertures. The body portion may be configured to extend around the respective one of the surgical instruments to force the respective one of the surgical instruments toward the support bracket. The body portion may be elastically extended around the respective one of the surgical instruments from the end portions secured within the apertures.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
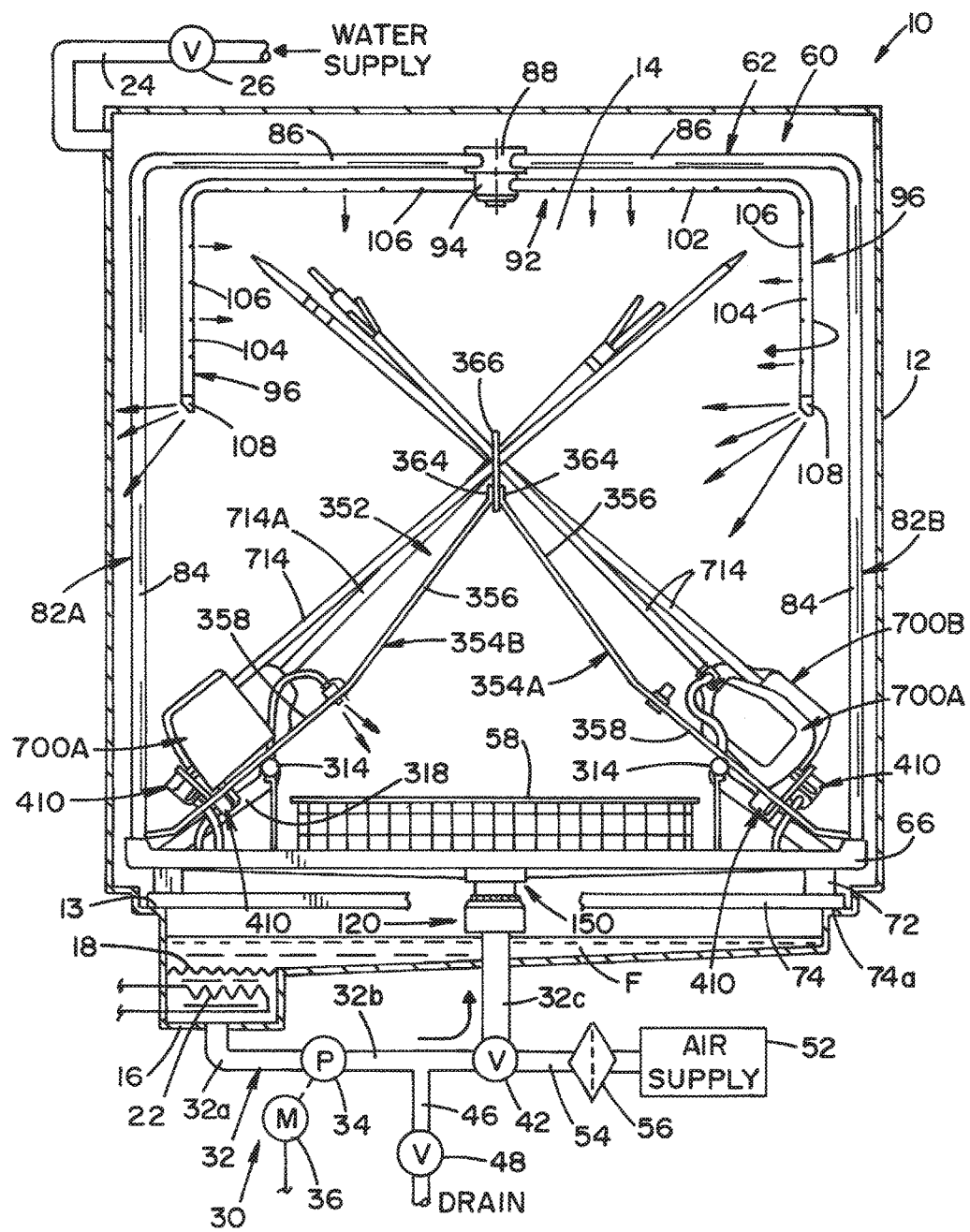
FIG. 1 is a sectional view of a schematically illustrated washer/disinfector showing therein a rack for washing/disinfecting wristed devices for a robotic surgical system, illustrating a preferred embodiment of the present invention.

Referring now to the drawings wherein the showings are for the purpose of illustrating a preferred embodiment of the invention only and not for the purpose of limiting same, FIG. 1 shows a washer/disinfector 10 for washing surgical instruments.

Washer/disinfector 10 includes a generally rectangular housing 12 that defines a washing chamber 14. A sump 16 is formed at the lower portion of housing 12 to collect fluids "F" used in washing chamber 14. A filter 18 is provided to filter fluids entering sump 16. A heater 22 is provided in sump 16 to warm fluids "F." A water inlet line 24 connects a water supply (not shown) to washing chamber 14. A valve 26 disposed in water inlet line 24 controls flow therethrough.

A first leg 32a of a fluid conduit 32 connects sump 16 to a pump 34 driven by a motor 36, as is schematically illustrated in FIG. 1. A second leg 32b of fluid conduit 32 connects pump 34 to a distribution valve 42 that controls flow from pump 34 to a third leg 32c of fluid conduit 32. Third leg 32c of fluid conduit 32 extends from distribution valve 42 through housing 12 into washing chamber 14. A fluid connection 120 is provided on a free end of third leg 32c of fluid conduit 32. Fluid conduit 32, pump 34, motor 36, and fluid connection 120 define a fluid recirculation system 30 for recirculating fluid "F" from sump 16 into washing chamber 14 through fluid conduit 32, as schematically illustrated by the arrows in FIG. 1 and as will be described in greater detail below.

A drain line 46 extends from secondary leg 326 of fluid conduit 32 to allow fluid to be drained from washing chamber 14. A valve 48 is disposed in drain line 46 to control flow therethrough.

Washer/disinfector 10 also includes a source 52 of air for conveying air into washing chamber 14 and, more particularly, through medical instruments within washing chamber 14 to facilitate drying the same. In FIG. 1, source 52 of air is schematically illustrated as an "Air Supply." The Air Supply may be pressurized from a building's air lines or a conventional blower (not shown). The Air Supply is connected to distribution valve 42 by an air conduit 54. An air filter 56, preferably a HEPA filter, is disposed in air conduit 54 to filter air flowing therethrough. Distribution valve 42 is preferably a three-way valve that controls whether liquid fluid or air is conveyed into washing chamber 14. A controller (not shown) controls the operations of washer/disinfector 10.

Figure 2:
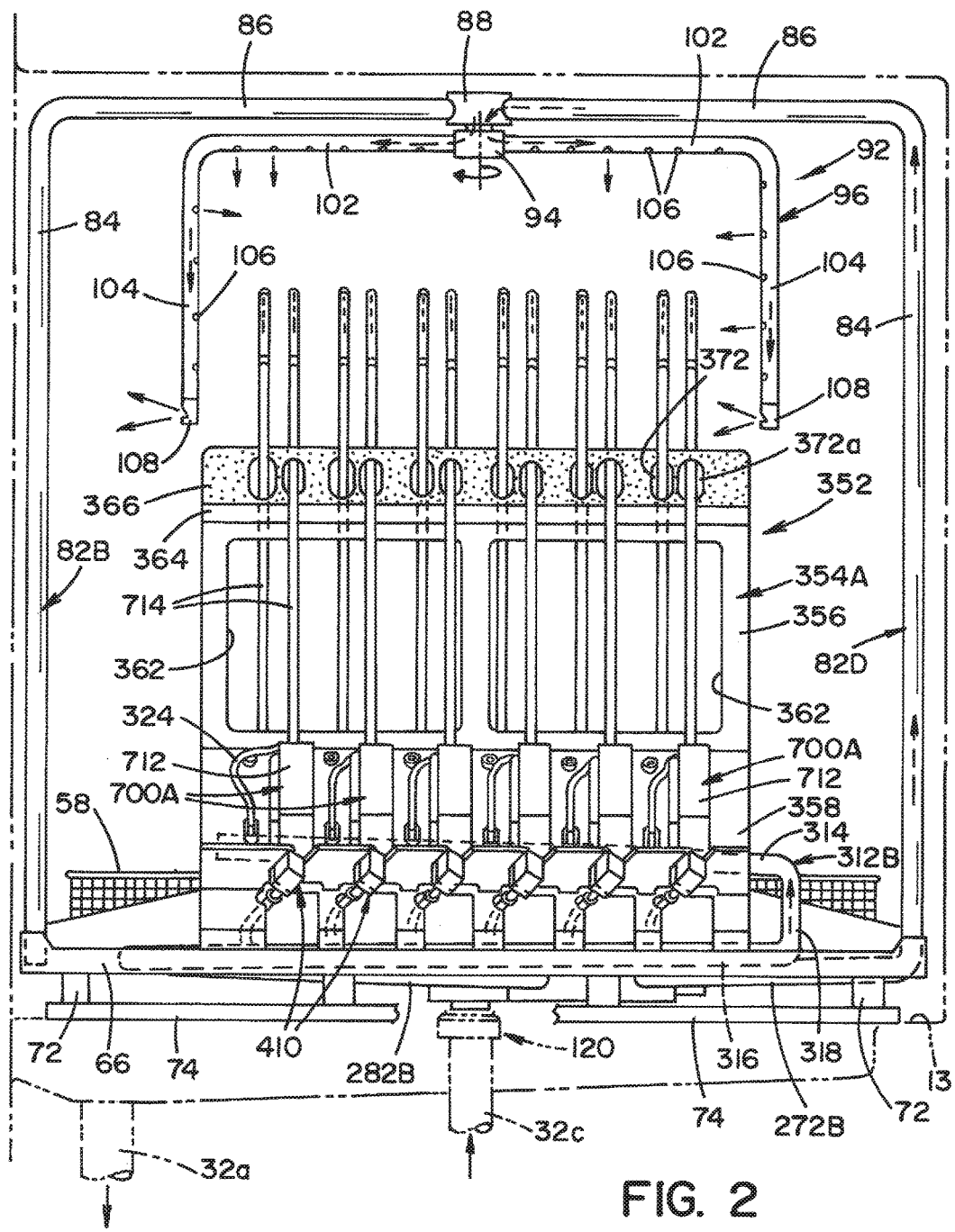
FIG. 2 is a side-elevational view of the rack shown in FIG. 1, showing a plurality of wristed devices mounted thereto.
Figure 5:
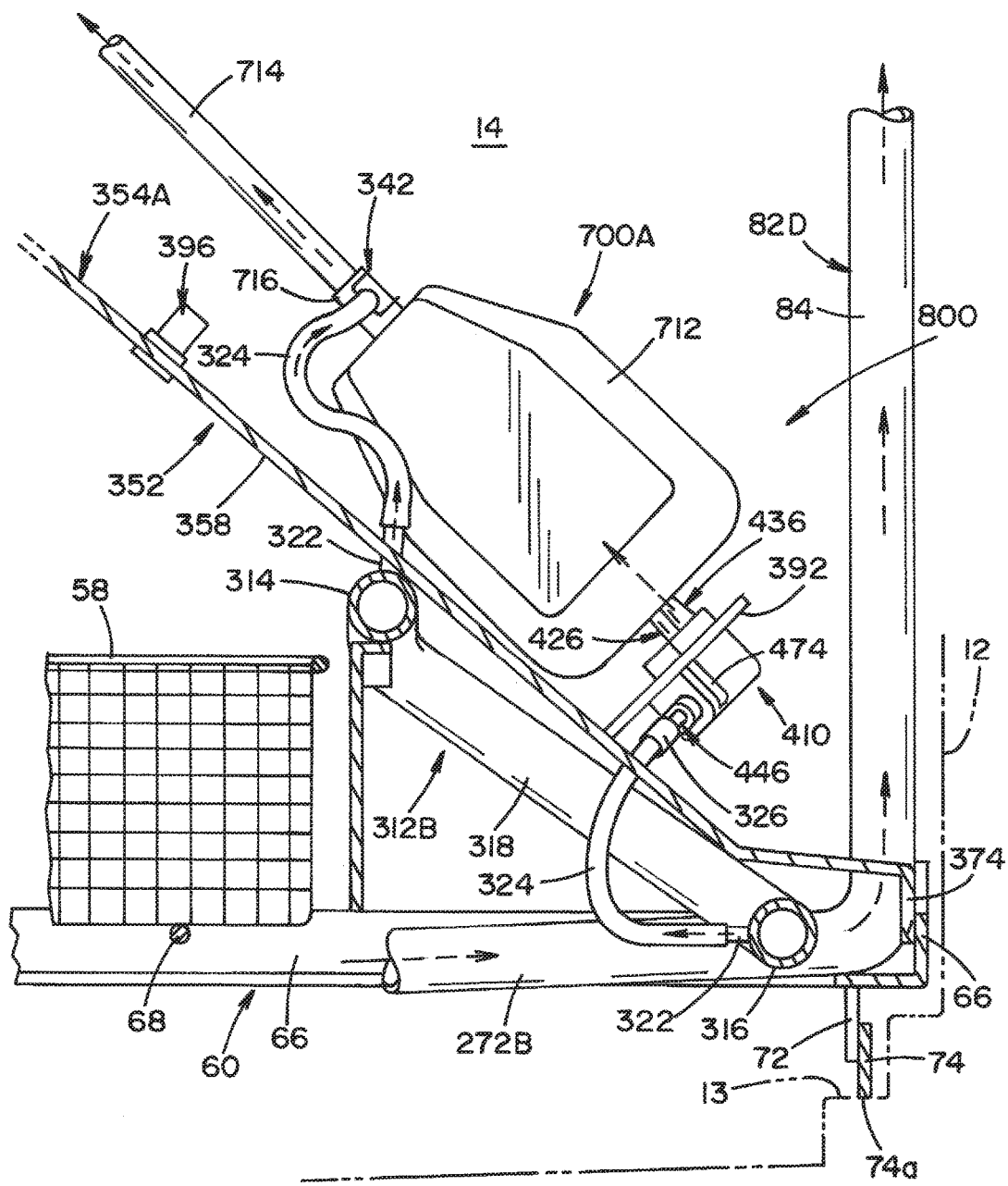
FIG. 5 is a side-elevational view, showing a first type of wristed device connected to an internal fluid circulation system and mounted to the rack using a securing system of a first example.
Figure 7:
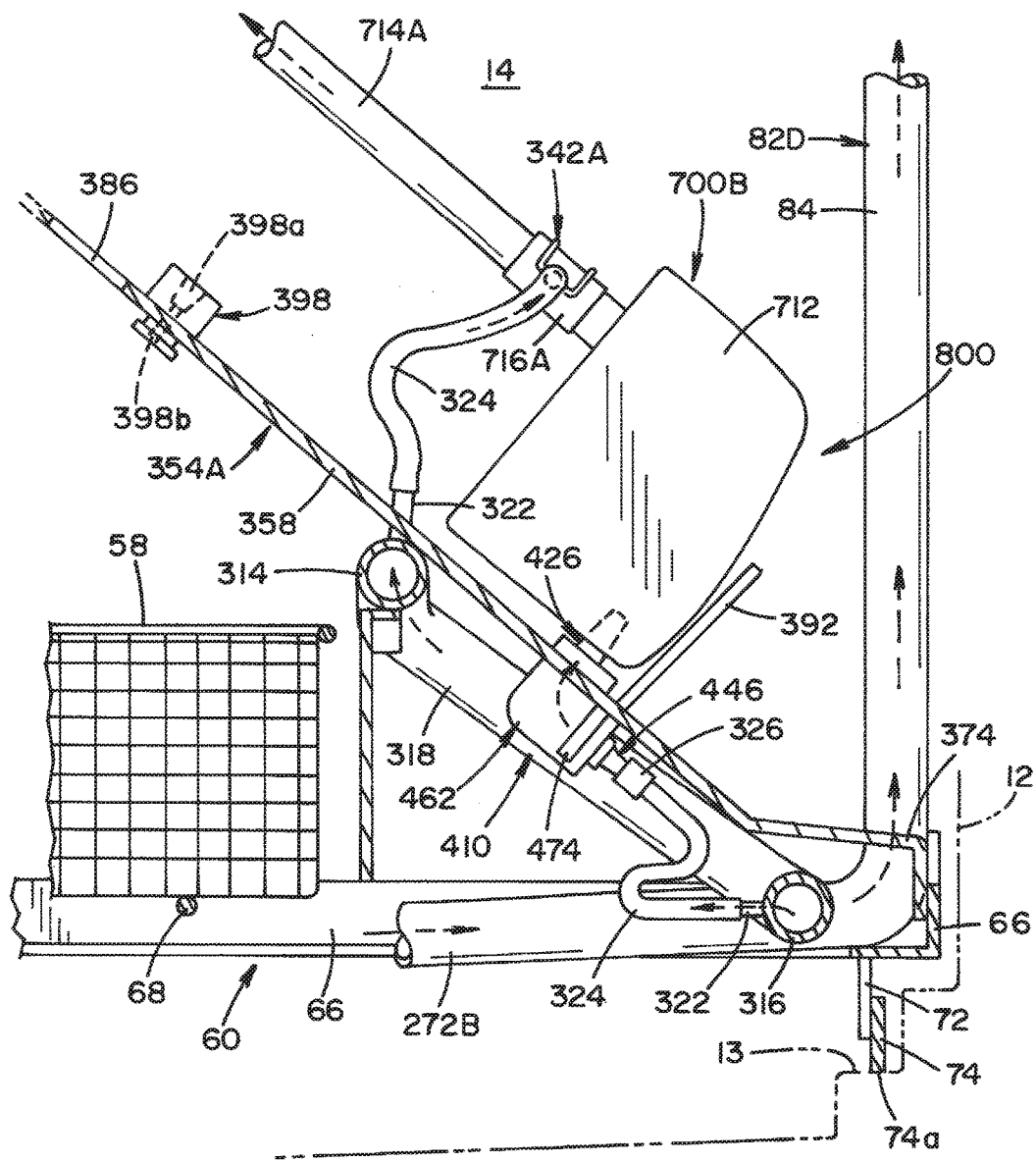
FIG. 7 is a side-sectional view, showing a second type of wristed device connected to an internal fluid circulation system and mounted to the rack using a securing system of a first example.
Figure 9:
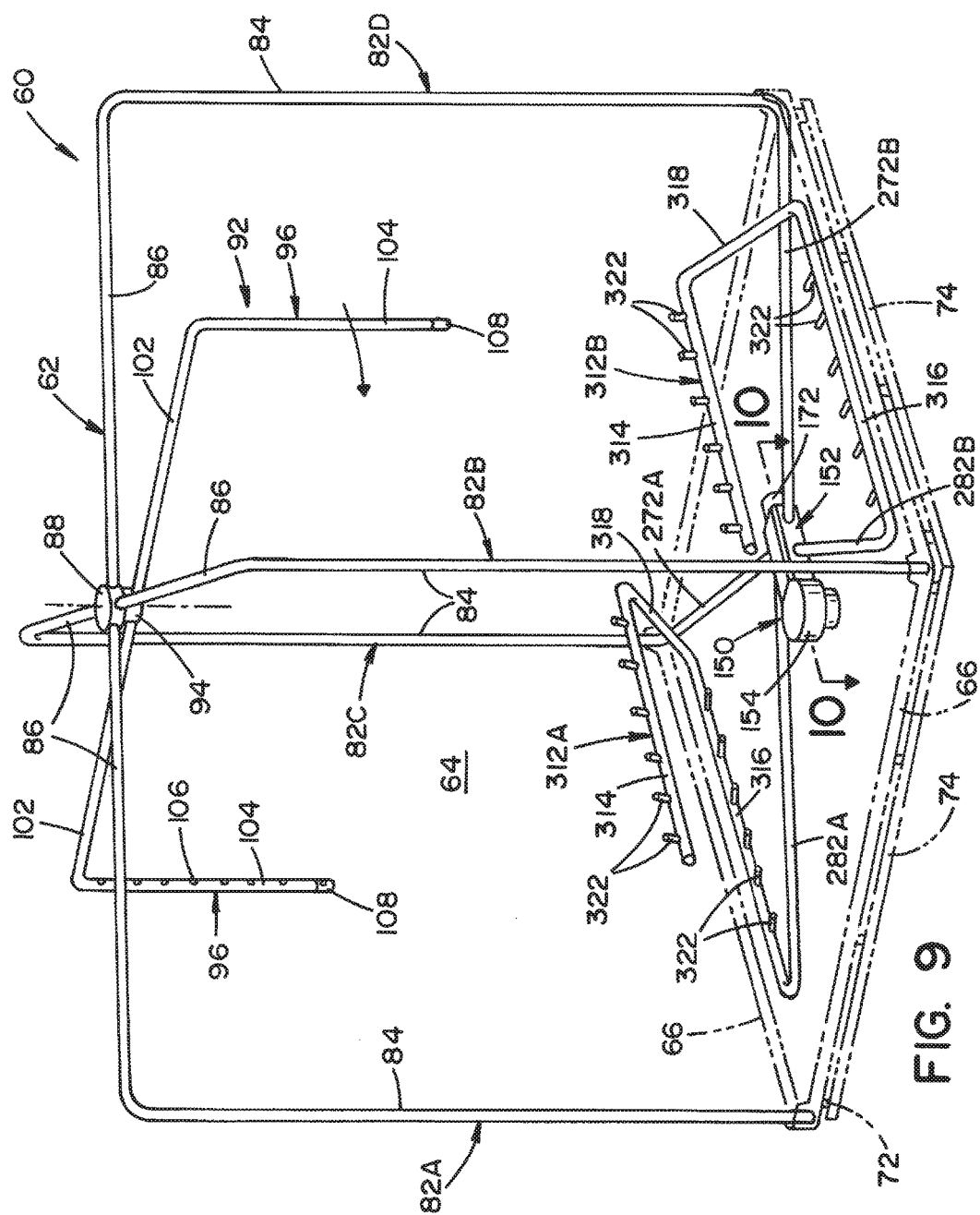
FIG. 9 is a perspective view of the rack (without the mounting assembly and the connectors), illustrating the overall structure of the rack.

Referring now to FIG. 9, a rack 60 for use in washer/disinfector 10 is best seen. Rack 60 is dimensioned to facilitate cleaning and disinfection of specialized robot surgical instruments, as shall be described in greater detail below. Rack 60 is generally comprised of a tubular frame 62 that defines an interior region or space 64. Frame 62 extends upward from a base 66. Base 66 is basically a rectangular frame. A plurality of spaced-apart rods 68 traverses two (2) sides of base 66 so as to define a support surface across the bottom of rack 60. (A rod 68 is shown in FIGS. 5 and 7.) A plurality of struts 72 extends downward from base 66. Struts 72 are attached to a sub-frame 74 that is also rectangular in shape but smaller in size than the base 66. (Base 66, struts 72, and sub-frame 74, best seen in FIGS. 2, 5, and 7, are shown in phantom in FIG. 9.) Sub-frame 74 of base 66 defines a downward-facing surface 74a. In the embodiment shown, sub-frame 74 is dimensioned to be movable along a shelf or ledge 13 formed by housing 12 near the bottom thereof. Rack 60 is dimensioned to be moved into and out of washing chamber 14 on ledge 13 and to rest thereon during a washing/disinfecting cycle. It is contemplated that rollers (not shown) could be provided within washing chamber 14 or on rack 60 to enable movement of the rack 60 more easily along the rollers into and out of washing chamber 14.

Four (4) L-shaped tubular sections 82A, 82B, 82C, and 82D extend upwardly from the corners of base 66. Each tubular section 82A, 82B, 82C, and 82D has a vertical leg portion 84 and a horizontal leg portion 86. The free ends of the horizontal leg portions 86 are joined at a centrally located, cylindrical block 88. Block 88 defines an inner cavity (not shown) that communicates with the inner passageways of tubular sections 82C, 82D. Together, the four (4) L-shaped tubular sections 82A, 82B, 82C, and 82D define a generally rectangular shape.

Mounted to the underside of block 88 is a U-shaped rotary spray arm assembly 92. Spray arm assembly 92 is comprised of a central hub 94 rotatably mounted to the underside of block 88 and two (2) L-shaped spray arms 96 extending radially outward from hub 94. Each spray arm 96 is formed to have a horizontal arm section 102 and a vertical arm section 104 that extend downward from the distal end of horizontal arm section 102. The inner ends of horizontal arm sections 102 extend from hub 94. Hub 94 is fluidly attached to block 88 to allow rotation of spray arms 96A, 96B about a generally vertical axis through block 88.

Each horizontal arm section 102 includes a plurality of spaced-apart spray nozzles or orifices 106 that are oriented downward to direct a spray of fluid into the central region of washing chamber 14. Each vertical arm section 104 includes a plurality of spaced-apart spray nozzles or orifices 106 that are directed inwardly to direct a spray of fluid between spray arms 96. In accordance with one aspect of the present invention, spray orifices 106 on vertical arm sections 104 are directed at an angle relative to the plane of spray orifices 106 on horizontal arm sections 102 no as not to interfere therewith. A spray nozzle 108 is provided at the free end of vertical arm sections 104 of spray arm 96A, 96B. Spray nozzle 108 on one of spray arms 96 is dimensioned to direct a spray of fluid "F" generally inwardly, while spray nozzle 108 on the other of spray arms 96 is dimensioned to direct a spray of fluid "F" generally outwardly. In this respect, the sprays from spray nozzles 108 are directed to cause spray assembly 92 to rotate.

Rack 60 is designed to be fluidly connected to a fluid circulation system 30 when rack 60 is disposed within washing chamber 14 of washer/disinfector 10.

To facilitate the fluid connection between rack 60 and fluid circulation system 30 of the washer/disinfector 10, a fluid coupling assembly 120 is provided on the end of third leg section 32c of fluid conduit 32 that extends into washing chamber 14. Fluid coupling assembly 120, best seen in FIG. 11, includes a fluid connection housing 122 that is generally cylindrical in shape at the end of third leg 32c of fluid conduit 32. Fluid connection housing 122 defines a cylindrical inner cavity 124 having an opened upper end and a lower end that is in fluid communication with fluid circulation system 30 of washer/disinfector 10 through conduit 32. Inner cavity 124 of fluid connection housing 122 is dimensioned to receive a cylindrical piston 126 therein.

Piston 126 is generally cup-shaped and has a cylindrical side wall 126a and a generally flat top wall 126b. An aperture 128 extends through top wall 126b of piston 126. An annular slot 132 is formed in the cylindrical outer surface of side wall 126a of piston 126. Slot 132 is dimensioned to receive an annular gasket 134 therein. Small apertures 136 extend through side walls 126a of piston 126 to communicate with annular slot 132 and the underside of gasket 134. As shown in the drawings, piston 126 is disposed within the inner cavity 124 of fluid connection housing 122 with the opened end of piston 126 facing downward toward the bottom of inner cavity 124. As will be described in greater detail below, when fluid or air pressure is applied to the underside of piston 126, piston 126 will be forced upward into engagement with a filter assembly 150 on rack 60.

Figure 11:
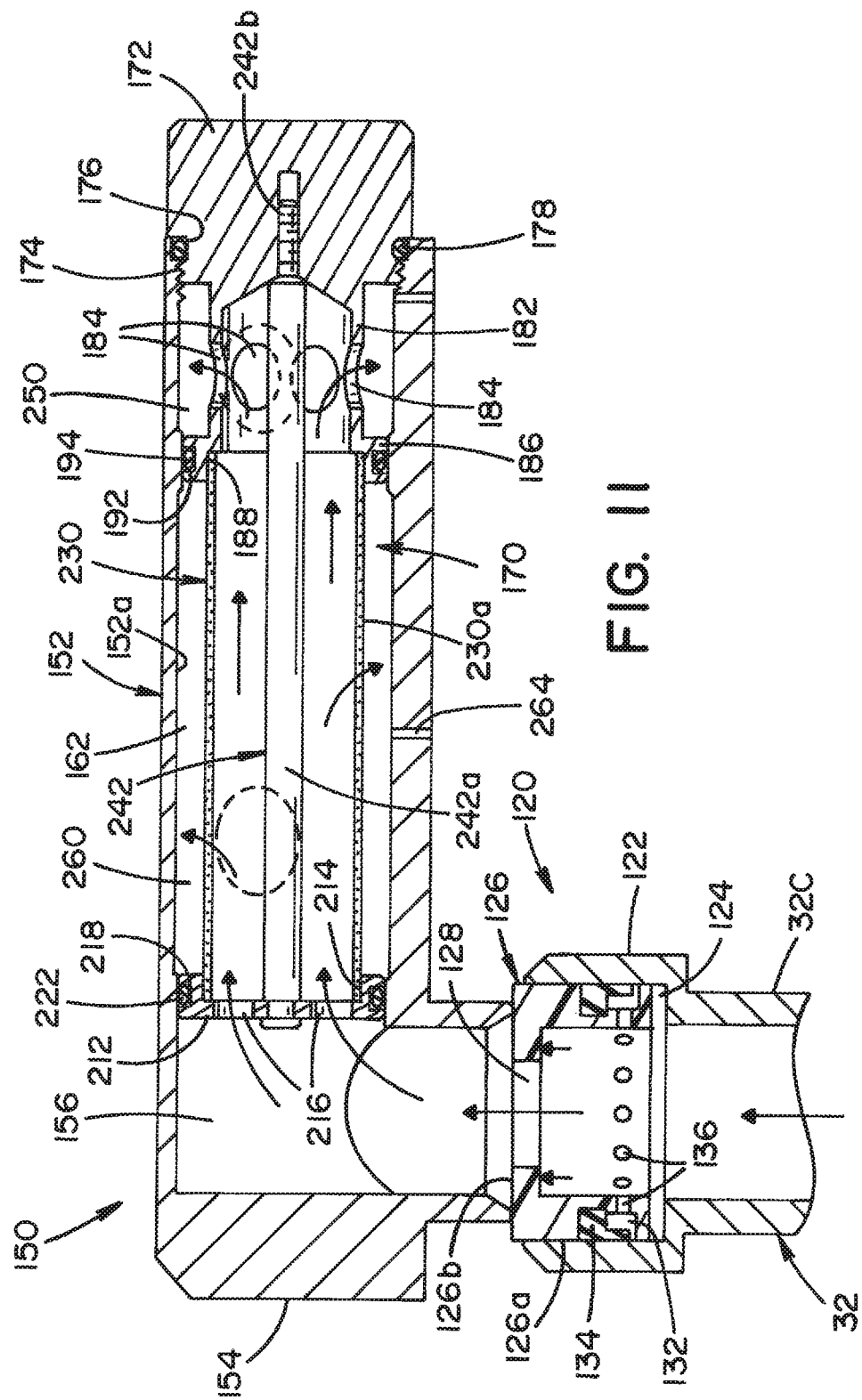
FIG. 11 is a sectional view taken along lines 11-11 of FIG. 10.

A cylindrical cavity 156 is formed within hub 154. Cavity 156 has an opened lower end that is dimensioned to be in registry with fluid coupling assembly 120 when rack 60 is within washing chamber 14, as illustrated in FIG. 11. As shown in the drawing, aperture 128 in piston 126 is aligned with cavity 156 when hub 154 is disposed in registry with fluid coupling assembly 120.

Figure 10:
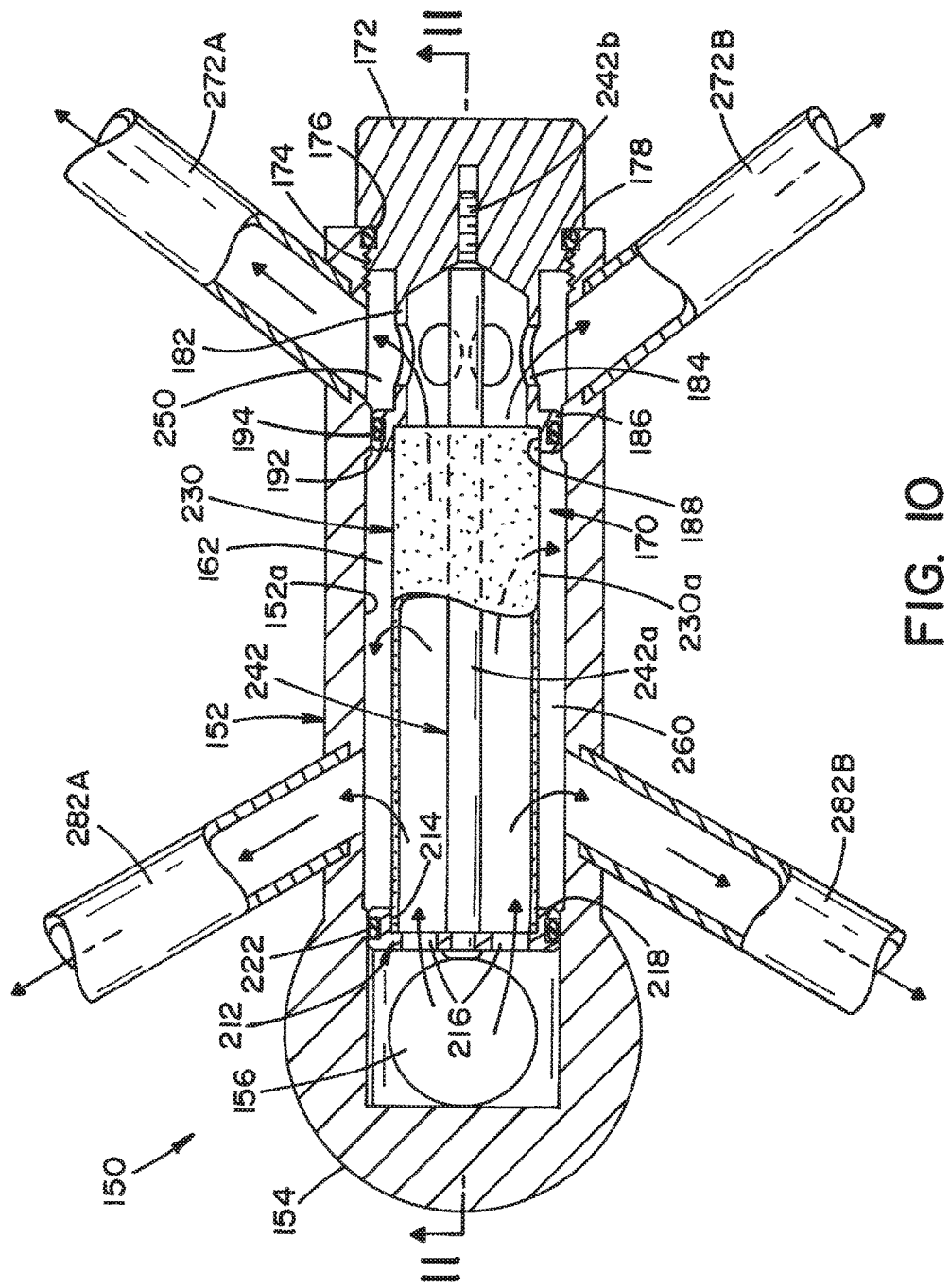
FIG. 10 is an enlarged sectional view taken along lines 10-10 of FIG. 9, showing a fluid distribution assembly and fluid flow paths therethrough.

Filter assembly 150, best seen in FIGS. 10 and 11, includes a filter housing 152 that extends from one side of a central hub 154. Housing 152 defines an elongated cylindrical inner chamber 162. One end of chamber 162 communicates with cavity 156 in hub 154. In the embodiment shown, filter housing 152 is integrally formed with hub 154.

A filter cartridge 170 is dimensioned to be received within chamber 162 of filter housing 152. Filter cartridge 170 is generally comprised of a cap 172, an end plate 212, and a cylindrical filter element 230 captured therebetween. Cap 172 is cylindrical in shape and has a smaller diameter threaded portion 174 extending therefrom. Threaded portion 174 is dimensioned to be matingly received by internal threads formed in the end of filter housing 152. An annular groove 176 is formed between cap 172 and threaded portion 174. Groove 176 is dimensioned to receive an annular, first seal element 178 therein. In the embodiment shown, first seal element 178 is a conventional O-ring.

A "necked-down" tubular portion 182 extends from threaded portion 174. Tubular portion 182 is smaller in diameter than threaded portion 174 and includes a plurality of spaced-apart openings 184 therethrough. An annular flange 186 is formed at the free end of tubular portion 182. An annular recess 188 is formed in the end of flange portion 186. An annular groove 192 is formed in the outer peripheral edge of flange portion 186 to receive a second seal element 194. Second seal element 194 is preferably an O-ring. End plate 212 is generally a flat cylindrical disk having a cylindrical recess 214 formed in one side thereof. Cylindrical recess 214 in end plate 212 is dimensioned to correspond to annular recess 188 formed in flange portion 186 of cap 172. A plurality of radially-spaced-apart apertures 216 is formed through end plate 212. An annular groove 218 is formed in the peripheral surface of end plate 212 to receive a third seal element 222. In the embodiment shown, end plate 212 and flange portion 186 of cap 172 are dimensioned to have like diameters, wherein the second and third seal elements 194, 222 are identical in diameter.

Cylindrical filter element 230 is received within the one end of annular recess 188 formed in flange portion 186 of cap 172. The other end of filter element 230 is received within cylindrical recess 214 in end plate 212. Filter element 230 is captured in place between cap 172 and end plate 212 by an elongated fastener 242 that extends through a centrally located opening in end plate 212 and extends into a threaded bore in cap 172. In the embodiment shown, fastener 242 is an elongated cap screw having a shank portion 242a and a threaded portion 242b at the end thereof. Together, filter element 230, end plate 212, and cap 172 form filter cartridge 170.

In accordance with one aspect of the present invention, filter element 230 is capable of filtering particles finer than filter element 18 in circulation system 30 of washer/disinfector 10. In a preferred embodiment, filter element 230 is a metal screen filter. In a more preferred embodiment, filter element 230 is formed of a sheet of stainless steel having pore openings of about 0.015 inch.

When filter cartridge 170 is inserted within filter housing 152, first, second and third sealing elements 178, 194, and 222 engage the inner surface of filter housing 152 to form fluid-tight seals therewith.

A first annular chamber 250 is defined between first and second seal elements 178, 194 and between tubular portion 182 of cap 172 and inner surface 152a of filter housing 152. A second annular chamber 260 is defined between second and third seal elements 194, 222 and between outer surface 230a of filter element 230 and inner surface 152a of filter housing 152.

As best seen in FIG. 11, cavity 156 in hub 154 is in fluid communication with the interior of filter element 230 through apertures 216 in end plate 212. The interior of filter element 230, in turn, is in fluid communication with the interior of cap 172 through the open end of filter element 230 and the opening in tubular portion 182 of cap 172. The interior of cap 172 is, therefore, in fluid communication with first annular chamber 250 through opening 184 in tubular portion 182 of cap 172.

The interior of filter element 230 is in fluid communication with second annular chamber 260 through the pores of filter element 230. Small drain holes 264, best seen in FIG. 11, are formed through filter housing 152 at the bottom of filter chamber 162.

Referring now to FIG. 10, a first pair of fluid distribution lines 272A, 272B is attached to filter housing 152 to be in fluid communication with first chamber 250 defined between first and second seal elements 178, 194. Fluid distribution lines 272A, 272B are attached to filter housing 152 and extend outwardly therefrom. Fluid distribution lines 272A, 272B extend from filter housing 152 to the lower end of L-shaped tubular sections 82C, 82D. Fluid distribution lines 272A, 272B are in fluid communication with the interior passageways of tubular sections 82C, 82D. In this respect, first annular chamber 250 of filter housing 152 is in fluid communication with spray orifices 106 and nozzles 108 on spray arms 96A, 96B on rotary spray assembly 92 through fluid distribution lines 272A, 272B, tubular sections 82C, 82D, hub 94 and spray arms 96A, 96B.

A second pair of fluid distribution lines 282A, 282B is attached to fluid housing 152 to be in fluid communication with second annular chamber 260 within filter housing 152. In this respect, fluid distribution lines 282A, 282B extend from filter housing 152 toward the outer edge of base 66. Each of fluid distribution lines 282A, 282B is attached to fluid manifolds 312A, 312B, respectively, that is disposed along a side of base 66.

Figure 8:
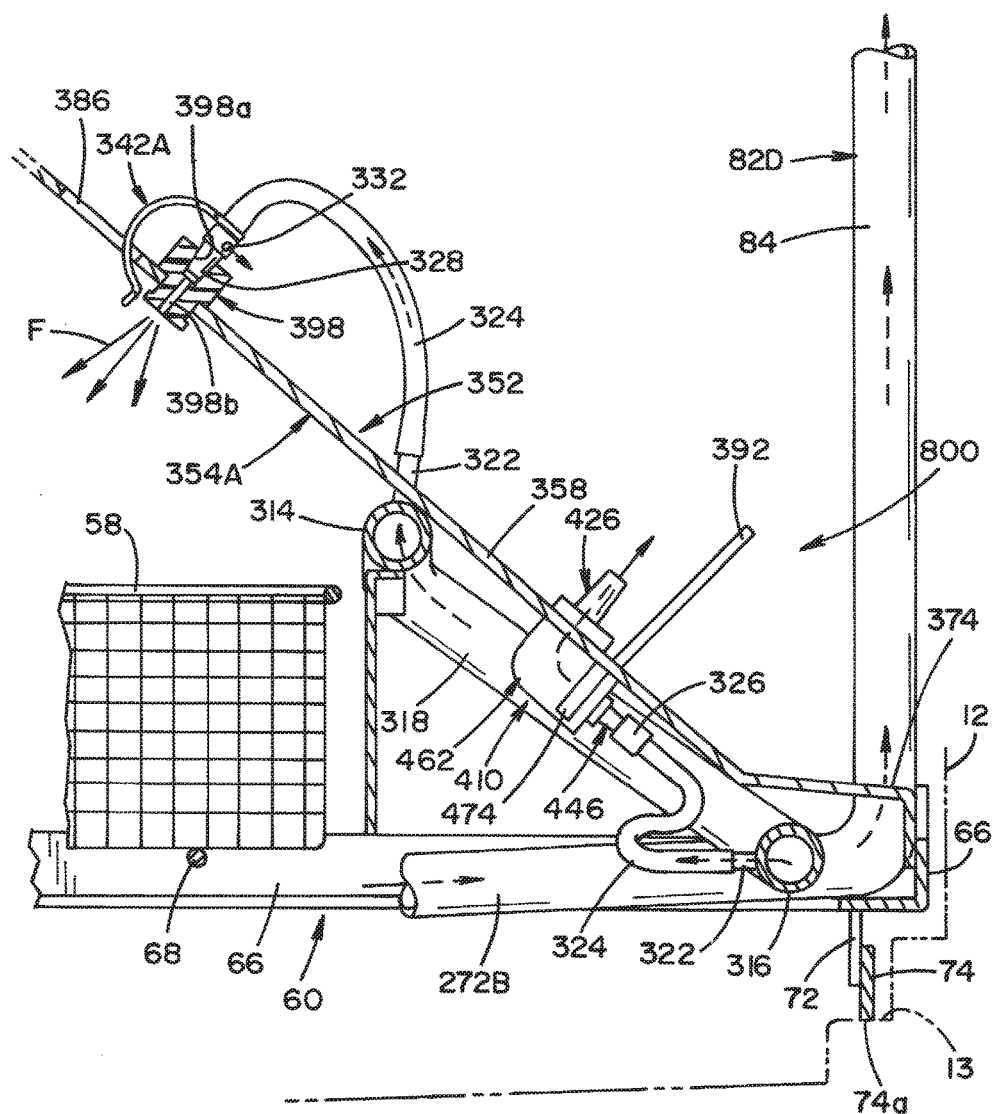
FIG. 8 is a side-elevational view, showing a connection hose attached to a second type of docking port on the rack.

As illustrated FIGS. 5, 7, and 8, distribution lines 272A, 272B, 282A, 282B are sloped slightly toward filter assembly 150 to facilitate draining of fluids "F" from tubular sections 82C, 82D and fluid manifolds 312A, 312B after certain operating phases of a washing/decontamination cycle, as shall be described in greater detail below. In the embodiment shown, each fluid manifold 312A, 312B is generally U-shaped and has an elongated upper leg section 314 connected to an elongated lower leg section 316 by an intermediate leg section 318. In the embodiment shown, upper and lower leg sections 314, 316 are generally parallel to each other and lie in a common plane. The plane of leg sections 314, 316 is inclined toward the center of rack 60. Upper leg sections 314 are disposed above the bottom of rack 60 and inwardly from one side thereof lower leg sections 316 are generally disposed near a lower edge of rack 60, as best seen in FIG. 9. Fluid distribution lines 282A, 282B are connected to fluid manifolds 312A, 312B, respectively, to be in fluid communication with the interior passageway found therein.

Figure 6:
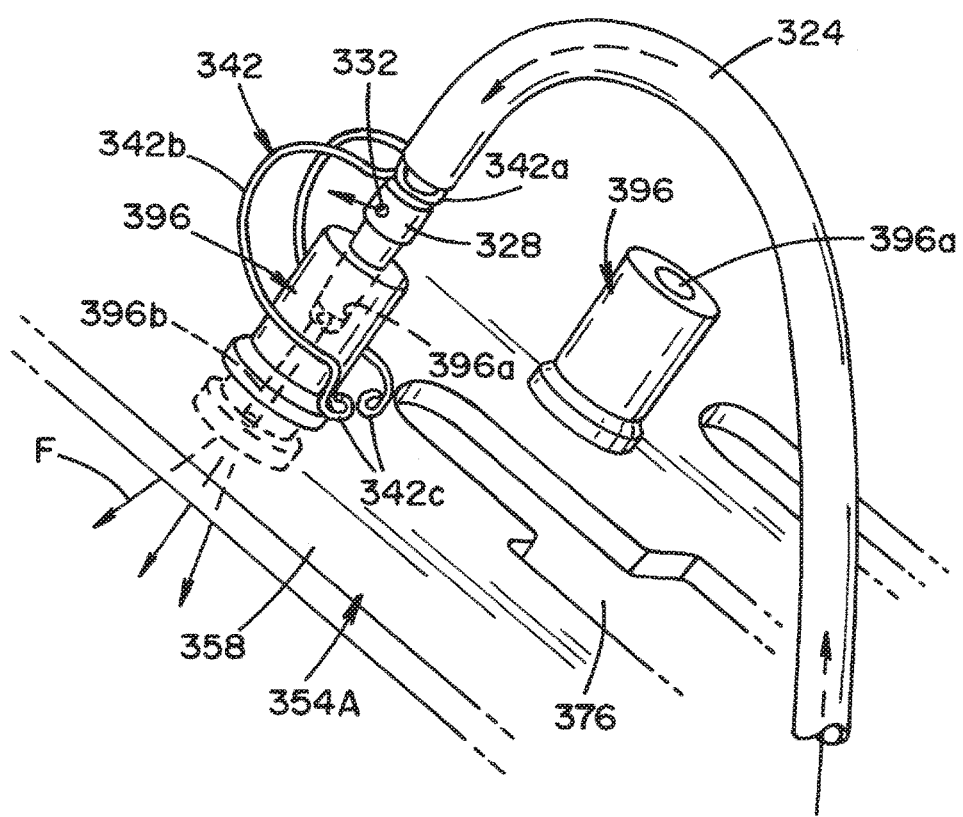
FIG. 6 is a perspective view of a connection hose attached to a first type of docking port on the rack.

A plurality of spaced-apart nipples 322 is attached along upper leg sections 314 of fluid manifolds 312A, 312B. Similarly, a plurality of spaced-apart nipples 322 is attached to lower leg sections 316 of fluid manifolds 312A, 312B. In the embodiment shown, six (6) nipples 322 are attached to each leg section 314, 316 of fluid manifolds 312A, 312B. Connection hoses 324 are attached to each nipple 322 on fluid manifolds 312A, 312B. Connection hoses 324 are formed of a flexible material, preferably, a polymer material. Female fittings 326 are attached to the ends of the connection hoses 324 that are attached to lower leg sections 316 of fluid manifolds 321A, 312B. Male fittings 328 are attached to the ends of connection hoses 324 that are attached to upper leg sections 314 of fluid manifolds 312A, 312B. As best seen in FIG. 6, a small hole 332 is formed in and through male fittings 328, as shall be described in greater detail below.

Each connection hose 324 attached to upper leg sections 314 of fluid manifolds 312A, 312B also includes a mounting clip 342, best seen in FIG. 6. Mounting clip 342 includes a loop or coil 342a at one end and two spaced-apart arcuate legs 342b that extend from loop or coil 342a. The loop or coil 342a is dimensioned to clamp onto male fitting 328 and to secure mounting clip 342 to male fitting 328. It is also contemplated that coil or loop 342a could be dimensioned to capture and secure the end of connecting hose 324 onto male fitting 328. In the embodiment shown, the ends of arcuate legs 342b are coiled into eyelets 342c to avoid sharp edges.

Mounting clip 342 is preferably formed of a non-corrosive spring metal material, such as, by way of example and not limitation, stainless steel. In accordance with one aspect of the present invention, mounting clip 342 is provided in two sizes, as shall be described in greater detail below.

In FIGS. 3-5, 7, and 8, a securing system 800 of a first example is illustrated. Securing system 800 includes a support stand 352 provided for supporting the surgical instruments to be cleaned. In the embodiment shown, support stand 352, best seen in FIGS. 1-5, is comprised of two (2) panels 354A, 354B that are attached together along their upper edges. Panels 354A, 354B are basically mirror images of each other and, therefore, only one shall be described in detail. Each panel 354A, 354B has an upper portion 356 and a lower portion 358. Upper portion 356 has large cutouts or openings 362 formed therein to allow fluid to pass therethrough. A flange 364 is formed along the upper edges of each panel 354A, 354B. Flanges 364 are angled slightly relative to upper portion 356 of panels 354A, 354B. Flanges 364 are fastened to each other with a holder 366 captured and held therebetween. Holder 366 is an elongated, generally flat member having a plurality of vertically aligned, spaced-apart obround slots 372 formed therein. As best seen in FIG. 2, some of the obround slots, designated 372a, are larger than other slots 372 to accommodate larger medical devices. Holder 366 is preferably formed of a polymeric material, such as, by way of example and not limitation, Teflon, so as not to scratch or damage the portions of medical instruments that will be placed therein, as shall be described below. When attached together, the panels 354A, 354B form a generally inverted V-shaped support stand 352, when viewed edgewise as shown in FIG. 1.

Figure 3:
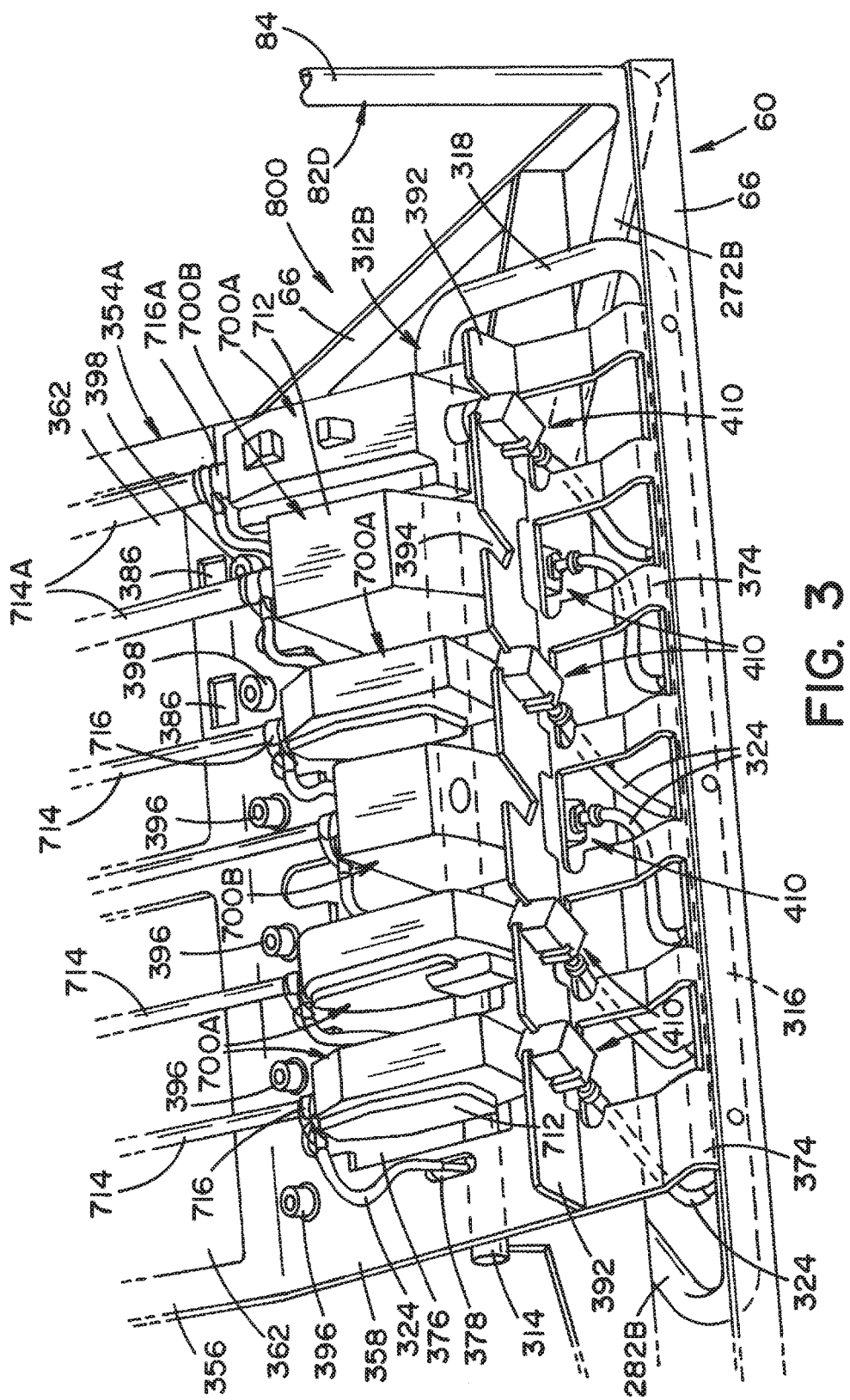
FIG. 3 is an enlarged perspective view of the rack, showing several different types of wristed devices, each device attached to a connector and mounted to the rack using a securing system of a first example.
Figure 4:
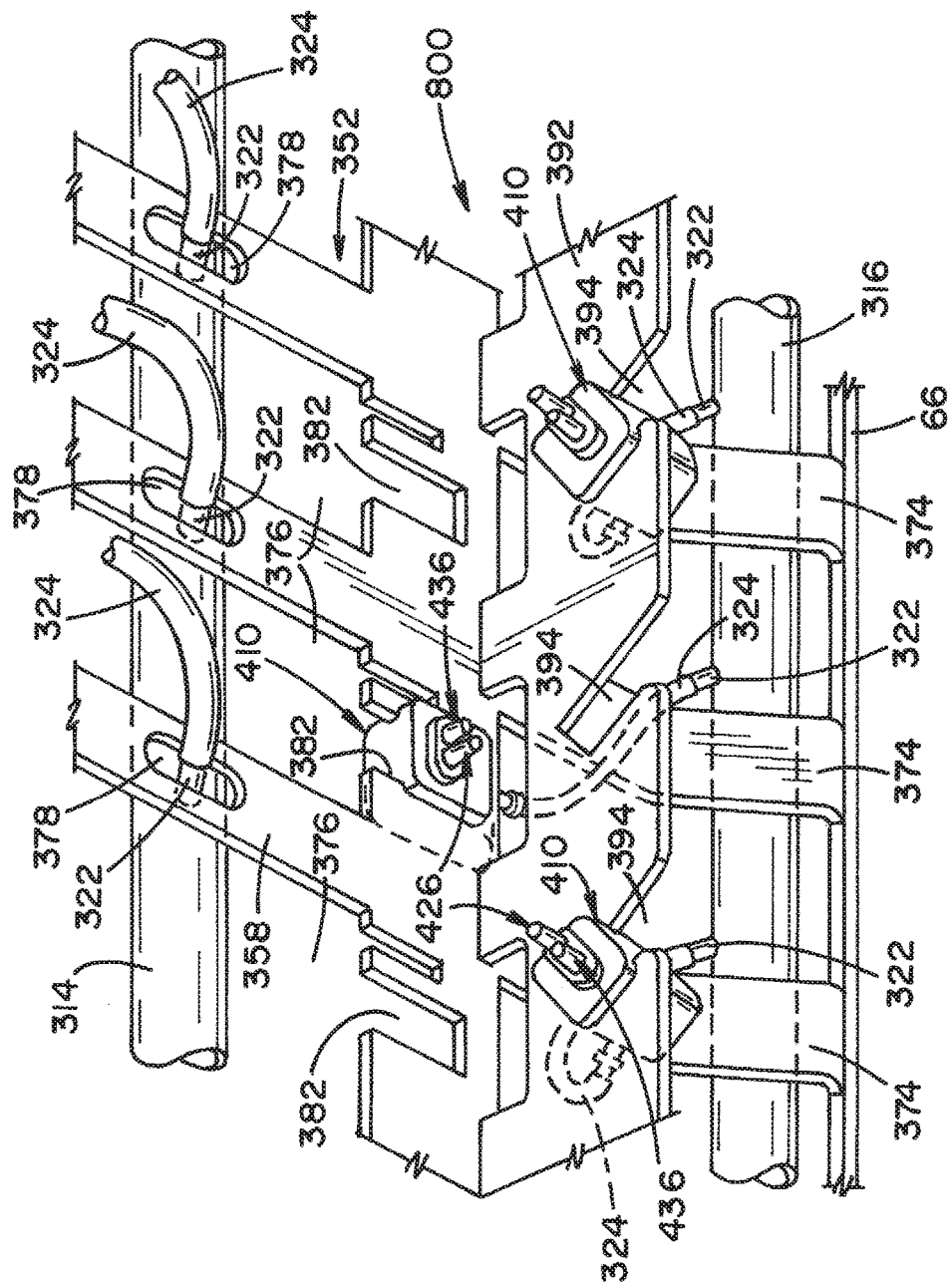
FIG. 4 is an enlarged perspective view, showing connectors attached to the rack using a securing system of a first example.

Referring now to FIGS. 3-5, lower portion 358 of panels 354A, 354B are best seen. The lower edges of panels 354A, 354B are formed to have legs 374 that attach to base 66 of rack 60, as best seen in FIG. 5. Large openings 376, best seen in FIG. 4, are formed in lower portion 358 of panels 354A, 354B to allow fluid "F" to flow therethrough. Smaller openings 378 are provided in lower portion 358 to allow nipples 322 and connection hoses 324 to pass therethrough. A plurality of spaced-apart slots 382 are formed in lower portion 358 of panels 354A, 354B. In the embodiment shown, six (6) slots 382 are formed in lower portion 358 to define "first connector mounting locations." A flat bracket 392 extends generally perpendicular from the upper surface of lower portion 358 of panels 354A, 354B. Bracket 392 includes a plurality of spaced-apart slots 394 that each defines a "second connector mounting location."

A plurality of docking ports 396, 398 is provided on panels 354A, 354B, as best seen in FIGS. 3 and 6. In the embodiment shown, a total of six (6) docking ports 396, 398 are provided on each panel 354A, 354B. A docking port 396, 398 is provided for each associated pair of first and second mounting locations. Docking port 396, as best seen in FIG. 6, is basically a cylindrical post mounted through an opening in panel 354A (or 354B). An opening extends axially through docking port 396. The opening through docking port 396 has a first portion 396a dimensioned to receive male fitting 328 on a connection hose 324 and a second portion 396b, smaller in size than first portion 396a, that is dimensioned to produce a spray of fluid "F" on the underside of panel 354A (or 354B), as will be described in greater detail below.

Docking port 398 is similar to docking port 396, but is slightly shorter in length and larger in diameter. Docking port 398 is a cylindrical post mounted through an opening in panel 354A (or 354B). An axial opening through docking port 398 has a first portion 398a dimensioned to receive male fitting 328 on a connection hose 324 and a second portion 398b dimensioned to produce a spray of fluid "F" on the underside of panel 354A (or 354B). An opening 386, best seen in FIGS. 7 and 8, is provided adjacent, i.e., above, each mounting dock 398.

As best seen in FIG. 1, a wire tray 58 is provided to be positioned beneath support stand 352 in the opening defined thereby. Tray 58 is supported in rack 60 by rods 68 that extend between the sides of base 66.

Figure 12:
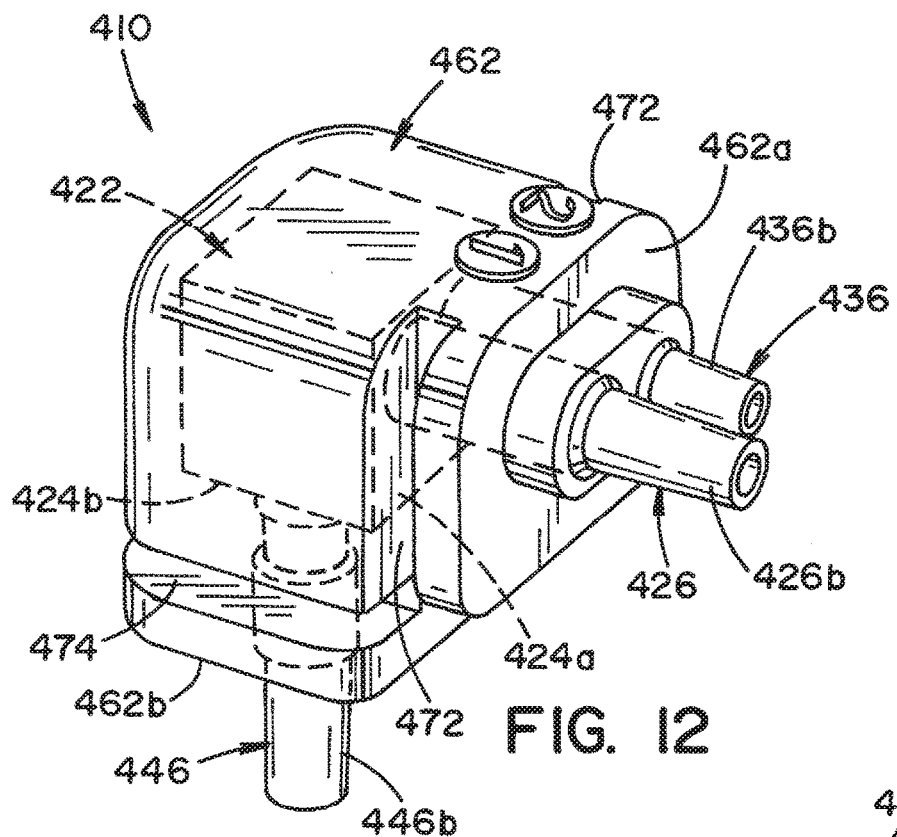
FIG. 12 is a perspective view, showing one end of a universal connector for connecting a wristed device to the fluid distribution system of the rack.
Figure 13:
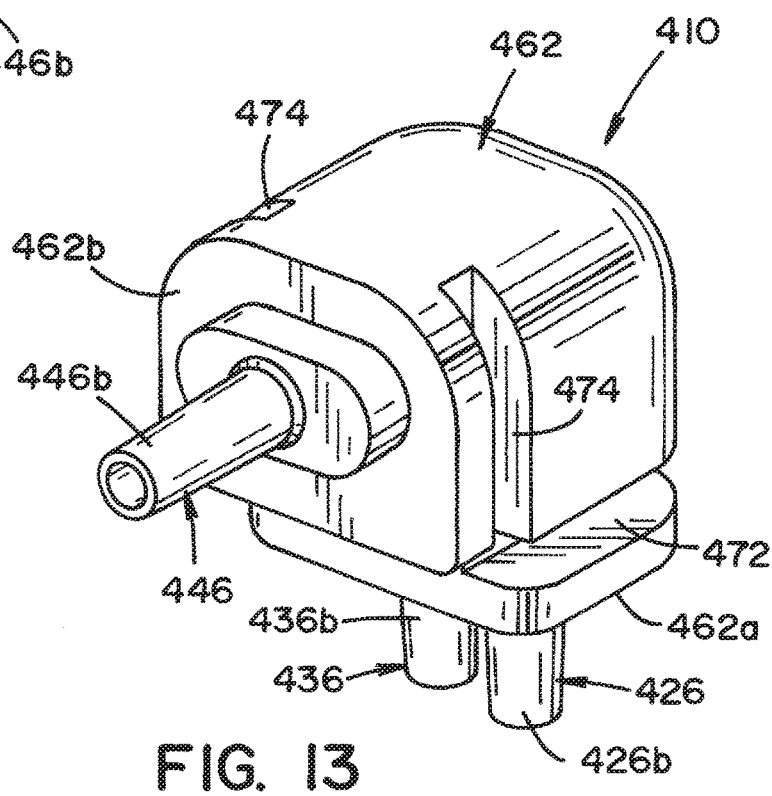
FIG. 13 is a perspective view, showing another end of the universal connector shown in FIG. 12.
Figure 14:
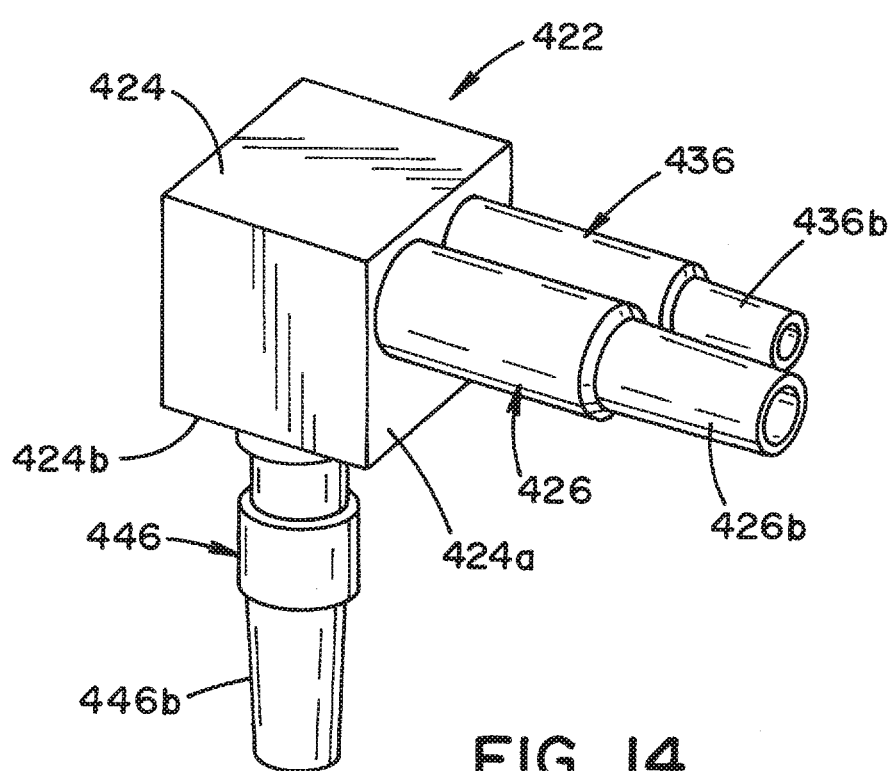
FIG. 14 is a perspective view of a rigid distribution box that is contained within the universal connector shown in FIGS. 12 and 13.
Figure 15:
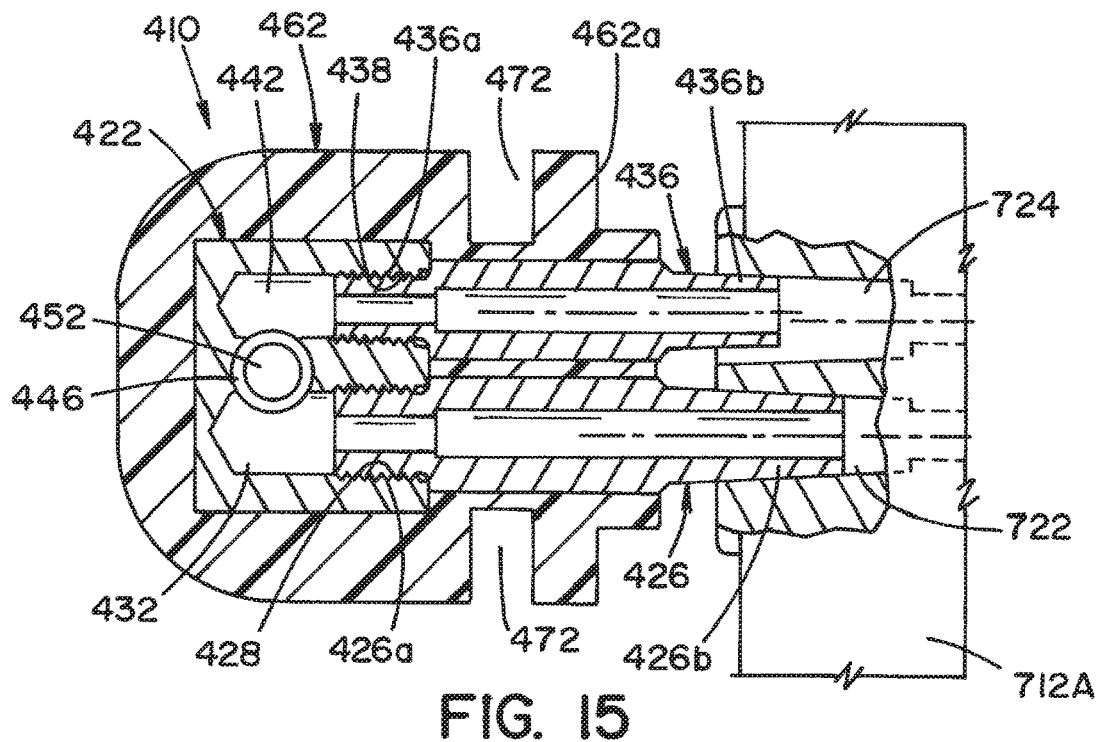
FIG. 15 is a sectional view, showing the universal connector shown in FIGS. 12 and 13 connected to ports on a first type of wristed device.
Figure 16:
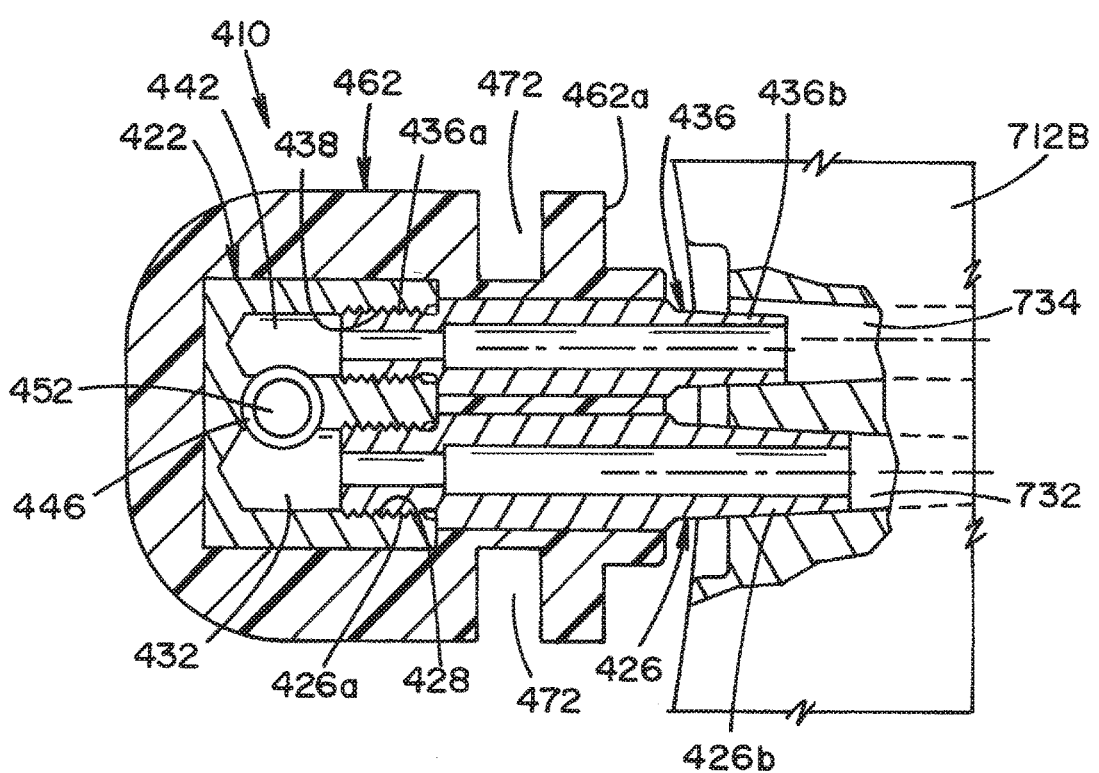
FIG. 16 is a sectional view, showing the universal connector shown in FIGS. 12 and 13 connected to ports on a second type of wristed device.

Referring now to FIGS. 12-14, a connector 410 for connecting connection hoses 324 to surgical instruments is best seen. Connector 410 is generally comprised of an inner conduit assembly 422 encased within an outer block or shell 462 formed of a resilient elastomeric material. Inner conduit assembly 422, best seen in FIG. 14, includes a distribution box 424. In the embodiment shown, distribution box 424 is generally rectangular in shape. A first tubular fitting 426 is attached to a first face 424a of distribution box 424. First tubular fitting 426 has a threaded end 426a (best seen in FIGS. 15 and 16) dimensioned to be received by internal threads 428 on a bored opening 432 that extends into distribution box 424. A second end 426b of first tubular fitting 426 has a slight taper, as best seen in FIG. 15. A second tubular fitting 436 is attached to first face 424a of distribution box 424. Second tubular fitting 436 has a threaded end 436a dimensioned to be received by internal threads 438 on a second bored opening 442 that extends into distribution box 424. A second end 436b of tubular fitting 436 has a slight taper. First and second tubular fittings 426, 436 extend generally parallel to each other, side-by-side from first face 424a of distribution box 424. As best seen in FIG. 14, first tubular fitting 426 is longer and larger in diameter than second tubular fitting 436. A third tubular fitting 446 is attached to a second face 424b of distribution box 424. In the embodiment shown, second face 424b of distribution box 424 is generally perpendicular to first face 424a. In this respect, third tubular fining 446 extends perpendicular to first and second tubular fittings, 426, 436. Like first and second tubular fittings 426, 436, third tubular fitting 446 has a threaded end 446a dimensioned to be received by internal threads (not shown) on a third bored opening 452 (best seen in FIGS. 15 and 16) that extends into distribution box 424. The other end 446b of third tubular fitting 446 is also slightly tapered. As best seen in FIGS. 15 and 16, third bored opening 453 extending into distribution box 424 intersects first and second bored openings 432, 442 that receive first and second tubular fittings 426, 436, respectively. In this respect, the passageways defined by the three tubular fittings 426, 436, 446 are in communication with each other within distribution box 424.

As indicated above, conduit assembly 422 is encased within an outer shell 462 of elastomeric material. In a preferred embodiment, the elastomeric material is formed of a silica material. Outer shell 462 includes a first end face 462a and a second end face 462b. First and second tubular fittings 426, 436 extend through first end face 462a of shell 462, and third tubular fitting 446 extends through second end face 462b in shell 462. In a preferred embodiment, first, second, and third tubular fittings 426, 436, 446 are tapered, male Luer fittings.

Slots 472 are formed on opposite sides of shell 462 of connector 410. In the embodiment shown, slots 472 are coplanar and generally parallel to first end face 462a of shell 462. Similarly, a second pair of slots 474 is formed adjacent to second end face 462b of shell 462. Slots 474 are coplanar and generally parallel to second end face 462b. Slots 472, 474 are dimensioned to allow connector 410 to be attached to brackets 392 and panels 354A, 354B of the support stand 352 by sliding connector 410 into slots 382, 394 formed on panels 354A, 354B and brackets 392, respectively. In this respect, connector 410 may be attached in one of two positions (orientations) on support stand 352, i.e., connector 410 may be mounted onto panels 354A, 354B or connector 410 may be mounted to bracket 392. Moreover, connector 410 may be mounted in two orientations, namely, a first orientation wherein connector 410 is mounted to brackets 392 or panels 354A, 354B using first pair of slots 472 or in a second orientation wherein connector 410 is mounted to panels 354A, 354B or bracket 392 using second pair of slots 474.

Referring now to the use and operation of the present invention, rack 60 is adapted for use in washing and disinfecting wristed medical instruments used on robotic surgical platforms, such as a daVinci® surgical platform. Such wristed instruments (hereinafter referred to as the "EndoWrist devices") typically include a control housing having dedicated injection ports or connectors thereon. An elongated shaft containing intricate cables and couplings extends from the control housing to a wrist assembly having a tip end. The control housing is designed for connection to a robotic surgical platform. Connection of the EndoWrist device to the surgical platform facilitates manipulation of the wrist end by means of control cables and connectors that extend through the shaft of the EndoWrist device. Currently, several different types or models of EndoWrist devices exist. Each model of an EndoWrist device may have a different type of control housing, and each control housing may have different ports at different locations thereon.

The port locations on a control housing of one EndoWrist device may vary slightly from the port locations on another EndoWrist device. In other words, one model of an EndoWrist device may have a slightly different spacing between ports than another model. One model of an EndoWrist device may have a "flush port" on the axial end of the control housing, whereas another model may have a "flush port" on the side of the control housing or at a location at the junction where the shaft extends from the control housing.

Rack 60, according to the present invention, is designed to accommodate different models of EndoWrist devices simultaneously within washer/disinfector 10.

Following a surgical procedure, an EndoWrist device is removed from the surgical platform. Each EndoWrist device is placed upon rack 60 by inserting the wristed end through one of the vertically aligned obround slots 372, 372a of holder 366 of support stand 352. FIG. 2 illustrates rack 60 holding twelve (12) like EndoWrist devices, designated 700A.

EndoWrist device 700A is a type having "flush ports" on the axial end surface of a control housing 712. EndoWrist device 700A is connected to a universal connector 410 by positioning first and second tubular fittings 426, 436 that extend from first face 462a of universal connector 410 into the ports 722, 724 in control housing 712. FIG. 15 schematically illustrates how connector 410 might attach to flush ports 722, 724 of a control housing 712A of one type of EndoWrist device. As illustrated in the drawing, first tubular fitting 426 is dimensioned to snugly fit within flush port 722 of control housing 712 and form a positive seal therewith. Typically, port 722 of control housing connects to an inner tube or "straw" (not shown) that extends through control housing 712 and through tube 714. The straw extends up to the end of tube 714. In this respect, fluid F forced into an EndoWrist device 700A through flush port 722 would be forced through the inner "straw" to the tip of tube 714. Since the tip is sealed, the fluid F would be forced back down tube 714 toward control housing 712, thereby cleaning and flushing the wires and cables that extend through tube 714 to the mechanical gripping devices on the end thereof.

In accordance with the present invention, second tubular fitting 436, which is shorter and smaller in diameter than first tubular fitting 426, is disposed on connector 410 so that tapered end 436b of second tubular fitting 436 may be partially insertable into flush port 724 of control housing 712A.

As noted above, different models of the EndoWrist device may have slightly different port spacings and positions on control housing 712. FIG. 16 schematically illustrates how connector 410 might attach to flush ports 732, 734 of a control housing 712B of a second type of EndoWrist device. In this second type of EndoWrist device, flush ports 732, 734 are farther apart than flush ports 722, 724 of the EndoWrist device shown in FIG. 15. Nevertheless, both first and second tubular fittings 426, 436 are insertable into flush ports 732, 734, respectively.

In accordance with one aspect of the present invention, first and second tubular fittings 426, 436 are dimensioned and spaced apart such that first and second tubular fittings 426 and 436 can be inserted into side-by-side flush ports on most, if not all, currently known models of EndoWrist devices, with one tubular fitting 426 snugly fitting into one flush port and the other tubular fitting 426 loosely fitting within the other flush port of an EndoWrist device.

With universal connector 410 attached to control housing 712 of EndoWrist device 700A, the wristed end of EndoWrist device 700A is positioned on support stand 352 by sliding the wristed free end of EndoWrist device 700A through one of the vertically aligned, obround, slots 372 on holder 366 of support stand 352. Universal connector 410, that is attached to the control housing, is then mounted onto support stand 352 by sliding universal connector 410 into a mounting location on bracket 392, as shown in FIG. 5. Shell 462 allows some flexibility to connector 410 to facilitate attachment of connector 410 to control housing 712. In this respect, slots 472 near end face 462a of universal connector 410 slide into slot 394 in bracket 392, thereby mounting universal connector 410 with EndoWrist device 700A onto support stand 352. With EndoWrist 700A device in place on rack 60, connector hose 324, that is associated with the mounting location, is attached to third tubular fitting 446 on second end face 426b of universal connector 410. As will be appreciated by those skilled in the art, connector hose 324 may be attached to universal connector 410 prior to the positioning of universal connector 410 in one of slots 394 on bracket 392. When connector hose 324 is attached to connector 410 as described above, housing 712 of EndoWrist device 700A is fluidly connected to lower leg section 316 of fluid manifold 312B. As illustrated in FIG. 5, EndoWrist device 700A may have a "flush port" located in elongated tube 714 or in collar 716 at the junction where elongated tube 714 and collar 716 extend from control housing 712. The associated connector hose 324 extending from upper leg section 314 of fluid manifold 312B would then be connected to the "flush port" on collar 716 of elongated tube 714 on control housing 712, as best seen in FIG. 5.

In this respect, clip 342 on the end of connection hose 324 would snap onto collar 716. More specifically, arcuate legs 342b would extend over and around collar 716 of control housing 712 to secure male fitting 328 on connection hose 324 in alignment and in engagement in the flush port of collar 716.

If EndoWrist device 700A did not have a "flush port" on elongated tube 714 or collar 716, the end of connection hose 324 would be "docked" in docking port 396 with male fitting 328 inserted in portion 396a of the axial opening therethrough. As illustrated in FIG. 6, arcuate legs 342b of mounting clip 342 are spaced apart such that they exert a clamping force on docking port 396 to maintain male fitting 328 within docking port 396.

An EndoWrist device may be a model having flush ports on the side of the control housing. FIG. 7 illustrates an EndoWrist device designated 700B having flush ports on the side of control housing 712. With this type of EndoWrist device, universal connector 410 would be attached to the side of control housing 712, with first and second tubular fittings 426, 436 of universal connector 410 attached to ports on the side of control housing 712. With EndoWrist device 700B, universal connector 410 would be mounted in a slot 382 on panel 354A that defines "a first mounting location." An associated connection hose 324 extending from the lower leg section 316 of fluid manifold 312 would be attached to universal connector 410.

Some EndoWrist devices, such as medical staplers, have elongated tubes that are larger in diameter than other EndoWrist devices. EndoWrist device 700B depicted in FIG. 7 is shown having an elongated tube 714A and collar 716A that are larger in diameter than those shown in FIG. 5. For EndoWrist devices having larger shafts 714A and collar 716A, a large mounting clip 342A is provided on connection hose 324. Mounting clip 342A is essentially the same, i.e., has the same shape and configuration, as mounting clip 342, but is merely larger in size to accommodate the larger sizes of tubes 714A and collars 716 that may exist on some type of EndoWrist devices. Rack 60 may include one or more connection hoses 324 to accommodate certain EndoWrist devices that may require larger mounting clips 342A.

Docking ports 398 and opening 386 are disposed adjacent connection hoses 324 having larger mounting clips 342A. If the EndoWrist device to be cleaned does not require connection to a connection hose 324 having a large mounting clip 342A, the connection hose 324 may be "docked" in docking port 398, as illustrated in FIG. 8, with mounting clip 342A extending the opening 386 and clamping onto, i.e., snapping onto, lower portion 358 of panel 354A and maintaining male fitting 328 in portion 398a of the hole extending through docking port 398.

FIG. 3 shows a plurality of different models of EndoWrist devices mounted onto support 352 and connected by connection hoses 324 to fluid manifold 312A. As indicated above, all connection hoses 324 may be attached to EndoWrist devices, or some connection hoses 324 may be attached to docking ports 396, 398. As shall be discussed in greater detail below, it is possible that some locations do not have EndoWrist devices attached thereto. In other words, washer/ disinfector 10 may operate without all locations on rack 60 having an EndoWrist device. In such situations, connection hoses 324 from upper leg sections 314 of fluid manifolds 312A, 312B would be "docked" to docking ports 396, 398. Connection hoses 324 from lower leg sections 316 would be attached to universal connector 410 which, in turn, would be mounted to support stand 352, as shown in FIG. 4.

In FIGS. 17-20, a securing system 900 of a second example is illustrated. Securing system 900 includes a support stand 952 provided for supporting the EndoWrist devices 700A, 700B to be cleaned. Support stand 952 is similar to support stand 352 of securing system 800 of the first example. Support stand 952 is illustrated as including panel 954A. Panel 954A is similar to panel 354A of securing system 800 of the first example. Panel 954A is illustrated to have a lower portion 958 that is similar to lower portion 358 of securing system 800 of the first example. The tower edge of panel 954A is formed to have a leg 974 that attaches to base 66 of rack 60. Leg 974 is similar to leg 374 of securing system 800 of the first example.

Figure 17:
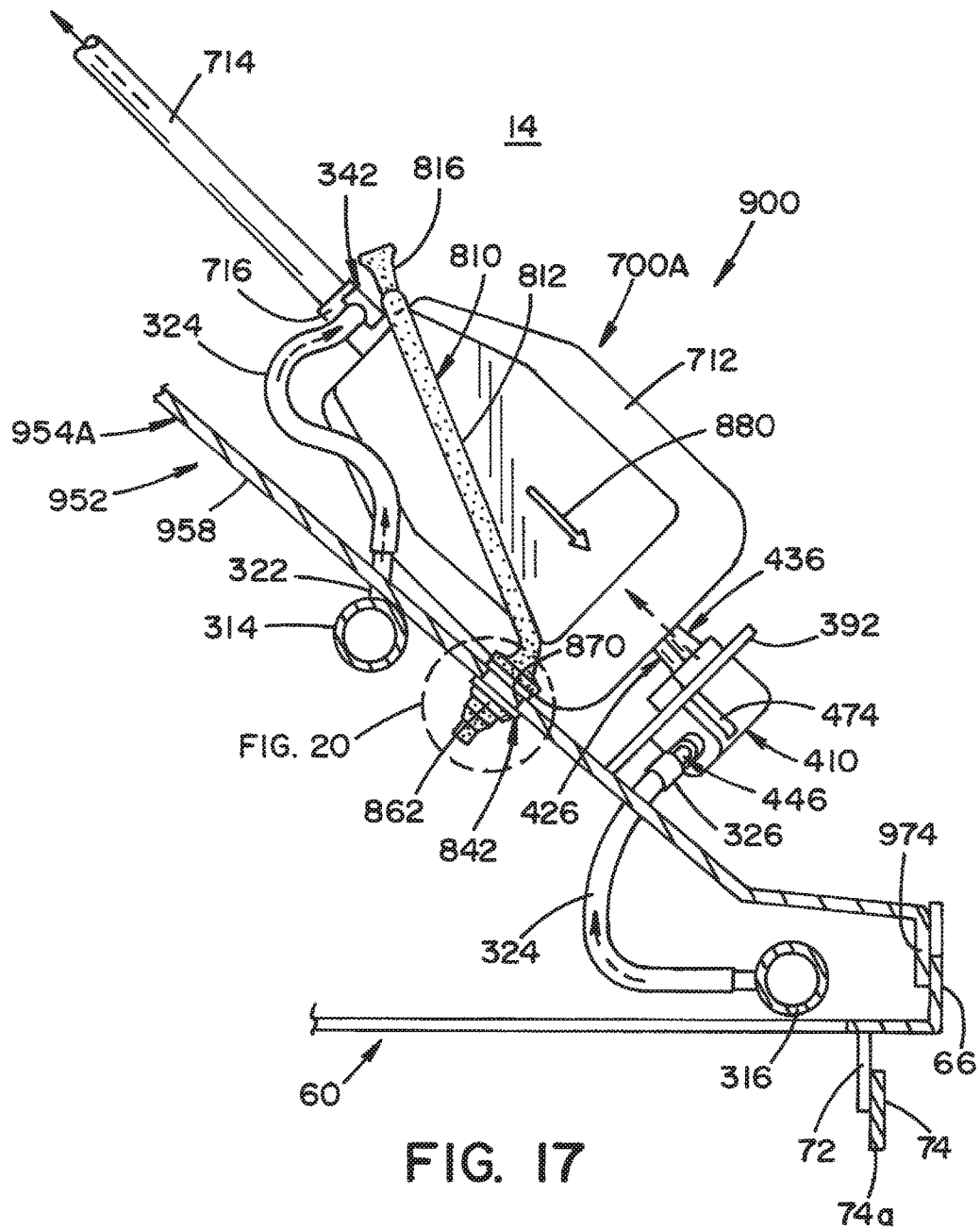
FIG. 17 is a side-sectional view, showing a first type of wristed device connected to an internal fluid circulation system and mounted to the rack using a securing system of a second example.
Figure 18:
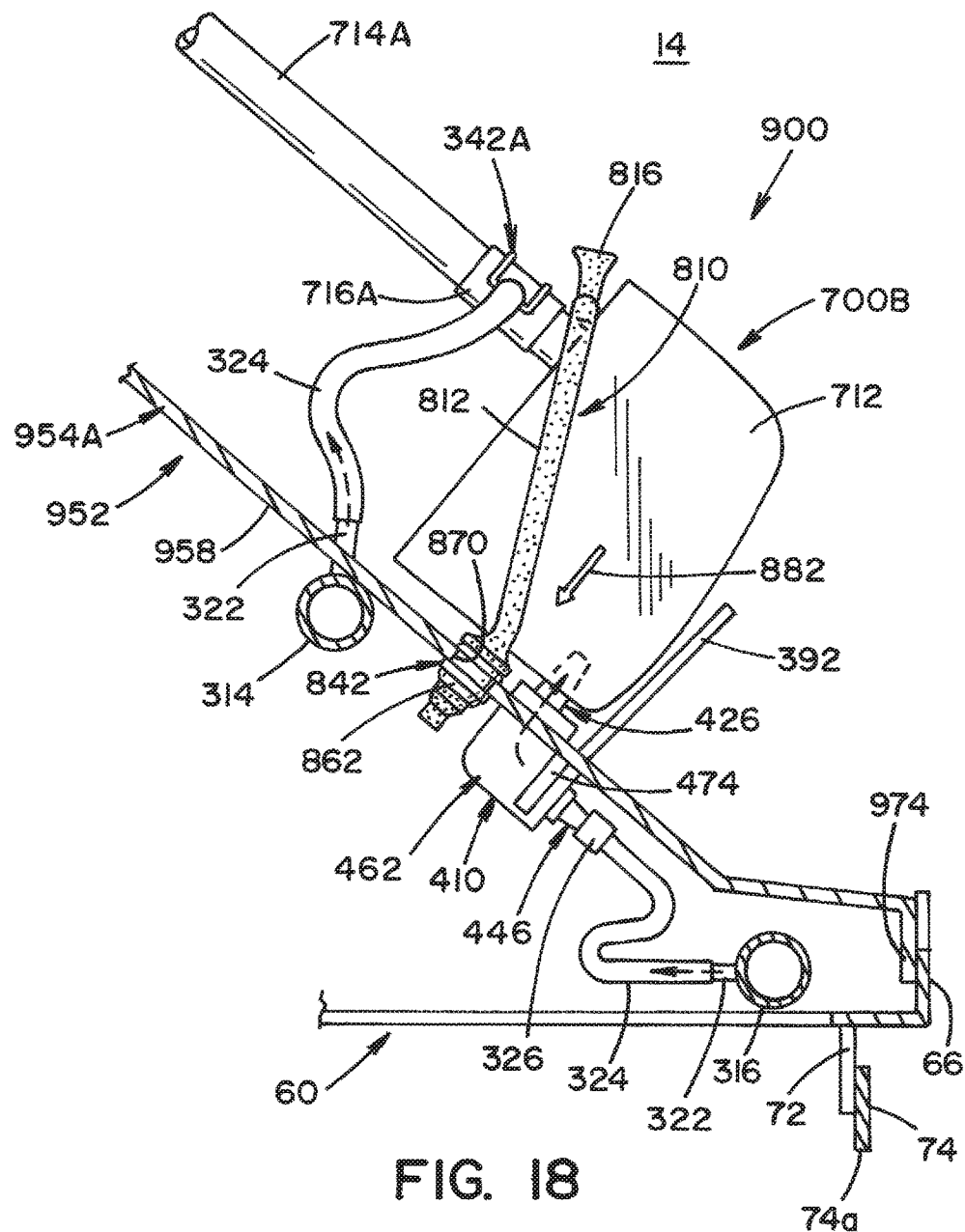
FIG. 18 is a side-sectional view, showing a second type of wristed device connected to an internal fluid circulation system and mounted to the rack using a securing system of a second example.
Figure 20:
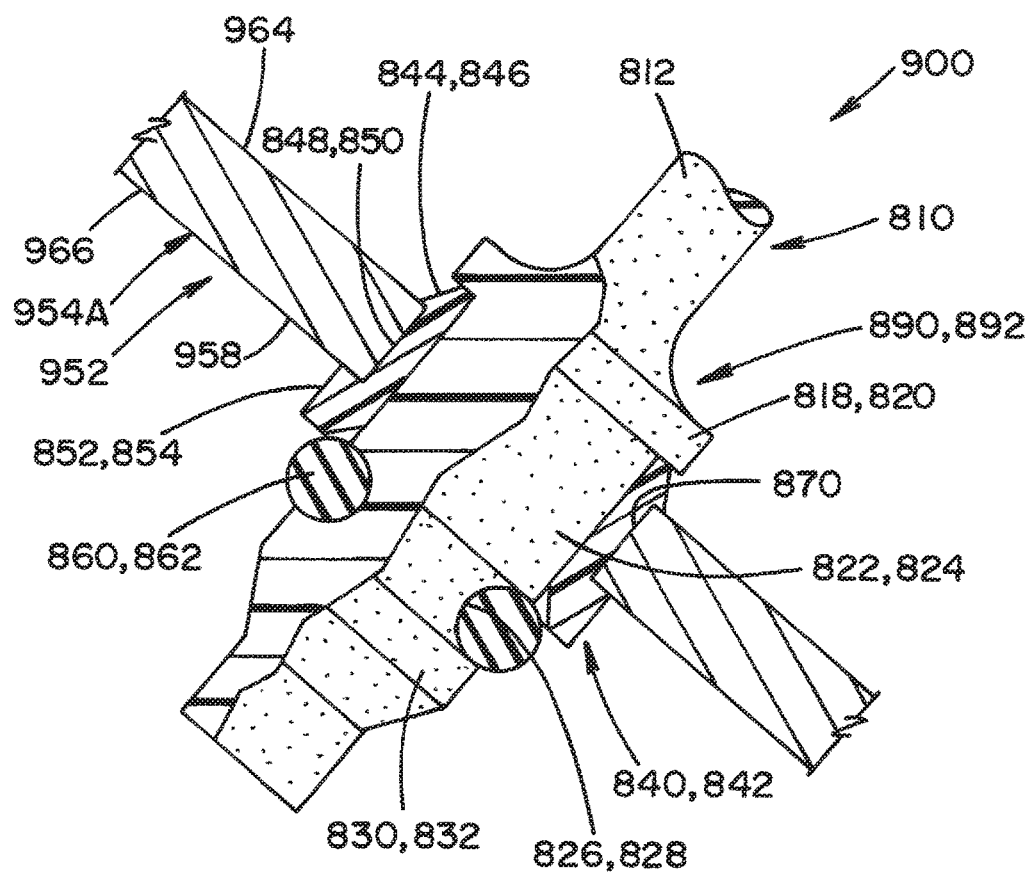
FIG. 20 is a cross-sectional view of a portion of the securing system of a second example illustrated in FIGS. 17 and 18.

However, in contrast with support stand 352, panel 354A, and lower portion 358, as is illustrated in FIG. 20, apertures 870 are formed in support stand 952, panel 954A, and lower portion 958 on opposite sides of EndoWrist device 700A in FIG. 17 and EndoWrist 700B in FIG. 18.

Further, securing system 900 of the second example includes a polymeric restraint 810 having elastic properties. Polymeric restraint 810 is configured to secure EndoWrist devices 700A, 700B to support stand 952. Polymeric restraint 810 is secured to support stand 952 within apertures 870 formed in panel 954A. When secured, polymeric restraint 810 can be elastically stretched around EndoWrist devices 700A, 700B to force EndoWrist devices 700A, 700B in respective directions 880, 882 toward flat bracket 392 and panel 954A. This inhibits movement of EndoWrist devices 700A, 700B or disconnection of EndoWrist devices 700A, 700B from connector 410 during high pressure cleaning that takes place within washer/disinfector 10.

Figure 19:
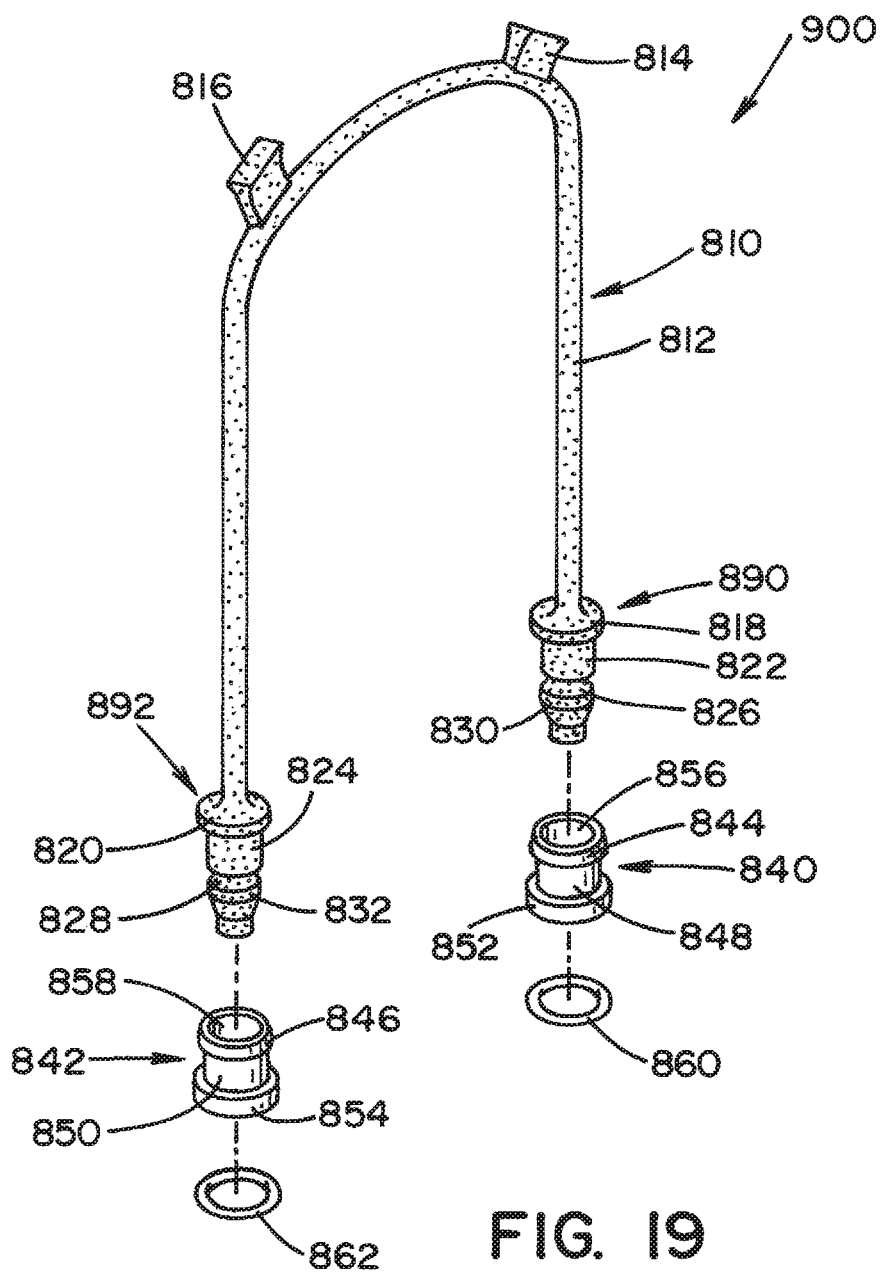
FIG. 19 is a perspective view of the securing system of a second example illustrated in FIGS. 17 and 18.

Polymeric restraint 810, best seen in FIG. 19, includes body 812, oppositely positioned positioning tabs 814, 816, and respective oppositely positioned restraint ends 890, 892. When ends 890, 892 are secured within apertures 870 of panel 954A, body 812 is configured to extend around EndoWrist devices 700A, 700B and secure EndoWrist devices 700A, 700B by respective forcing EndoWrist devices 700A, 700B toward flat bracket 392 and panel 954A. When ends 890, 892 of polymeric restraint 810 are secured within apertures 870, polymeric restraint 810 can be stretched around EndoWrist devices 700A, 700B using positioning tabs 814, 816. Polymeric restraint 810 secures EndoWrist devices 700A, 700B with force in respective directions 880, 882 that correspond with the design of EndoWrist devices 700A, 700B and the location at which ends 890, 892 of polymeric restraint 810 are secured within corresponding apertures 870.

Securing system 900 additionally includes panel conduits 840, 842 that are securely positioned through and within inner circumferences of corresponding apertures 870. Restraint ends 890, 892 of polymeric restraint 810 are structured to secure polymeric restraint 810 to panel 954A by respectively extending through securely positioned panel conduits 840, 842.

An example configuration of apertures 870, restraint ends 890, 892 and panel conduits 840, 842, respectively corresponding therewith, is illustrated in FIGS. 19 and 20. Panel conduits 840, 842 respectively include upper flanges 844, 846, panel channels 848, 850, and lower flanges 852, 854. Restraint ends 890, 892 respectively include body flanges 818, 820, tubular sections 822, 824, ring channels 826, 828, and ring flanges 830, 832.

Upper flanges 844, 846 and lower flanges 852, 854 are dimensioned to respectively contact top surface 964 and bottom surface 966 of panel 954A. Upper flanges 844, 846 and lower flanges 852, 854 have outer diameters that are greater than diameters of respective apertures 870. Panel channels 848, 850 are positioned between respective upper flanges 844, 846 and lower flanges 852, 854. Panel channels 848, 850 extend through apertures 870 and are positioned against apertures 870 formed within panel 954A. The outer diameters of upper flanges 844, 846 and lower flanges 852, 854 serve to secure respective panel conduits 840, 842 to panel 954A and maintain panel channels 848, 850 within respective apertures 870.

Tubular sections 822, 824 of ends 890, 892 project from body flanges 818, 820 away from body 812 and are dimensioned to be positioned within and through respective panel channels 848, 850. Body flanges 818, 820 are positioned adjacent to respective tubular sections 822, 824 and in contact with respective upper flanges 844, 846. Body flanges 818, 820 have greater diameters than top portions of respective upper flanges 844, 846 and, as a result, extend over upper flanges 844, 846. As a result of the dimensions of body flanges 818, 820 and tubular sections 822, 824, insertion of ring flanges 830, 832, ring channels, 826, 828, and tubular sections 822, 824 of respective ends 890, 892 into panel conduits 840, 842, can take place, as well as extension thereof through the panel conduits 890, 892. In addition, body flanges 818, 820 contact respective upper flanges 844, 846 of panel conduits 840, 842 to inhibit body 812 from extending through apertures 870 and panel conduits 840, 842.

On opposite respective sides of tubular sections 822, 824 from body flanges 818, 820, ring channels 826, 828 are formed within respective ends 890, 892 and between tubular sections 822, 824 and ring flanges 830, 832. Ring flanges 830, 832 form lower edges of respective ring channels 826, 828 and become narrower as they extend away from ring channels 826, 828. Tubular sections 822, 824 form upper edges of respective ring channels 826, 828.

Ring channels 826, 828 are dimensioned to accept respective ring flanges 860, 862 therein. Rings 860, 862 are polymeric in construction with elastic properties. Rings 860, 862 can be positioned and held within respective ring channels 826, 828 by the upper edges of ring channels 826, 828 formed by tubular sections 822, 824 and the lower edges of ring channels 826, 828 formed by ring flanges 830, 832. As a result of such positioning, rings 860, 862 contact respective lower flanges 852, 854 of panel conduits 840, 842, thereby inhibiting ends 890, 892 from being removed from panel conduits 840, 842 when body 812 is being stretched around EndoWrist devices 700A, 700B to secure the devices 700A, 700B by way of respective force 880, 882.

While securing system 900 is illustrated by FIGS. 17-20 as being applicable to EndoWrist devices 700A, 700B possessing the structure described and illustrated herein, embodiments described herein are not limited thereto. For example, securing system 900, along with flat bracket 392 and panel 954A, is configured to secure any EndoWrist independent of geometry or dimensions thereof.

With the EndoWrist devices 700A, 700B loaded onto support static 352, 952, rack 60 is positioned within washer/disinfector 10.

A system controller (not shown) controls the operation of washer/disinfector 10 and the various components thereof. A typical operation of washer/disinfector 10 includes a fill phase, an exposure phase, a rinse phase, and a drying phase.

The system controller initiates the fill phase of washer/disinfector 10. During a fill phase, water from an external source (not shown) fills sump 16. Once filled to a desired level, the system controller stops the flow of water into washing chamber 14. Heating element 22 within sump 16 is typically energized to heat water in sump 16. Chemicals are added to the water to form a deactivating fluid "F."

The system A second fluid flow path is defined through filter element 230 to second annular chamber 260. From second annular chamber 260, fluid "F" is directed by distribution lines 282A, 282B to U-shaped fluid manifolds 312A, 312B. From fluid manifolds 312A, 312B, fluid "F" is directed through connection hoses 324 that are, in turn, attached to housing 712 or shaft 714 of the EndoWrist devices 700A, 700B. Fluid "F" is forced into and through control housing 712, through elongated tubular shaft 714 of the EndoWrist devices 700A, 700B, and exits from the EndoWrist devices 700A, 700B at the wrist or free end thereof. Fluid "F" forced along this second fluid path is filtered by filter element 230 prior to entering control housing 712 of the EndoWrist device 700A, 700B. Although circulation system 30 of washer/disinfector 10 has filter 18 for filtering particles from fluid "F" flowing into sump 16, filter element 230 of filter cartridge 170 provides additional micro-filtering of fluid "F" directed to the interior of the EndoWrist devices 700A, 700B, thereby ensuring that only highly filtered fluids "F" are allowed to enter the interior cavities and passageway's of the intricate EndoWrist devices 700A, 700B. Fluid "F" directed to connection hoses 324 that are not connected to an EndoWrist device 700A, 700B are merely directed toward the center of rack 60 onto accessory devices that may be present in tray 58.

According to one aspect of the present invention, the pressure of the fluid "F" in fluid circulation system 30 is maintained between 30 and 60 psi. Preferably, the operating pressure of fluid circulation system 30 is between 50 and 60 psi. In this respect, 30 psi is the recommended cleaning pressure suggested by the manufacturer of the EndoWrist devices 700A, 700B, and 60 psi is the maximum cleaning pressure that can be applied to such devices. By operating near the upper end of the pressure range, a minimum cleaning pressure is still maintained throughout control housing 712 and elongated tubular portions of the EndoWrist devices 700A, 700B, despite the leaking that occurs at the connections between universal connectors 410 and the EndoWrist devices 700A, 700B and the fluid loss that occurs through unattached connection hoses 324. Still further, the higher operating pressure ensures that sufficient pressure to the interior portions of control housing 712 and tubular section 714 of the EndoWrist device 700A, 700B is maintained through filter element 230 along the second fluid path of fluid circulation system 30. Holes 332 in male fittings 328, of connection hoses 324 allow leakage of fluid "F" to prevent over-pressure conditions from reaching the inner section of the EndoWrist devices.

The exposure phase of the cleaning cycle lasts a predetermined period of time. Following the exposure phase, fluid "F" is drained from washer/disinfector 10. In this respect, the system controller causes valve 48 to move to an open position to allow fluid "F" within fluid circulation system 30 to drain therefrom. According to another aspect of the present invention, the configuration of rack 60, which basically holds the EndoWrist devices 700A, 700B in an inclined orientation, allows fluid "F" within the EndoWrist devices 700A, 700B to drain therefrom. Fluid "F" drains from the EndoWrist devices 700A, 700B back to fluid manifolds 312A, 312B and then back toward fluid coupling assembly 120. The slope in distribution lines 272A, 272B, 282A, 282B helps drain fluid "F" from rack 60 to filter assembly 150 and fluid coupling assembly 120. In this respect, when pressure of fluid circulation system 30 no longer exists, piston 126 beneath filter assembly 150 will drop back down, thereby allowing fluid "F" above this location to drain in washing chamber 14 from the EndoWrist devices 700A, 700B mounted to rack 60. Fluid "F" would then be collected in sump 16 and drained through drain line 46. Holes 264 in the bottom of fitter housing 152 help drain fluids from filter assembly 150.

Following the exposure phase, a rinse phase is initiated. A rinse phase of washer/disinfector 10 basically consists of a fill phase wherein clean, filtered water is introduced into sump 16 of washer/disinfector 10. This is followed by a circulation phase where the clean water is forced through the interior of the EndoWrist devices 700A, 700B, as described above. Similarly, the rinse water is sprayed onto the exterior of the EndoWrist devices 700A, 700B, as described above.

Following a rinse phase, the system controller again drains washer/disinfector 10 to remove rinse water from within the EndoWrist devices 700A, 700B and rack 60.

The system controller initiates a drying phase of washer/disinfector 10. The drying phase typically includes initiating a blower which circulates dry, heated air throughout the interior of washing chamber 14. In addition, dry, heated air is forced through fluid circulation system 30 to force dry, heated air along the second fluid flow path into control housing 712 of the EndoWrist devices 700A, 700B and through elongated tube section 714 thereof. Following the washing/disinfecting cycle, the EndoWrist devices 700A, 700B are disconnected from rack 60 and from universal connectors 410.

The present invention, thus, provides a rack 60 and a method of cleaning/disinfecting EndoWrist devices 700A, 700B in a repeatable manner that is more consistent and reproducible than manual cleaning. Washer/disinfector 10 allows operation at pressures exceeding the manufacturer's minimum 30 psig pressure, to ensure thorough cleaning within control housing 712 and tubular portion 714 of the EndoWrist device 700A, 700B. Enhanced cleaning of the wrist end of the EndoWrist device 700A, 700B is the result of spray orifices 106 and spray nozzles 108 directing cleaning fluid onto the wristed end of the EndoWrist device. The present invention further provides a single assembly that can facilitate washing of different models of EndoWrist devices 700A, 700B as a result of universal connector 410 that connects the EndoWrist devices 700A, 700B to fluid connection hoses 324 of fluid circulation system 30.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:
1. A rack for holding and washing surgical instruments in a washer/disinfector, comprising:
   a frame assembly having a plurality of tubular sections, said frame assembly defining an interior region configured to receive said surgical instruments for respective positioning therein, said frame assembly comprising a base from which said tubular sections extend;

a rotary spray arm mounted to said frame assembly, said spray arm having a plurality of spray nozzles configured to direct a fluid provided from said tubular sections toward said surgical instruments respectively positioned within said interior region;

a fluid inlet positioned on said frame assembly, said fluid inlet being configured to connect said frame assembly to a fluid circulation system in said washer/disinfector, said fluid inlet being further configured to provide said fluid to said tubular sections from said fluid circulation system;

a first fluid path defined from said fluid inlet to said spray nozzles through said tubular sections, the first fluid path being configured to direct said fluid from said fluid inlet to said spray nozzles;

a second fluid path defined from said fluid inlet to a plurality of connectors through said tubular sections, the second fluid path being configured to direct said fluid from said fluid inlet to said connectors, each of said connectors being configured to connect to a respective one of said surgical instruments and provide said fluid thereto;

a filter configured to filter said fluid from said fluid inlet; and a securing system configured to secure each of said surgical instruments in a predetermined orientation in said interior region, said securing system comprising:
  a support stand on which said surgical instruments are supported, said support stand being attached to said base, said support stand extending from said base into said interior region, said support stand comprising a plurality of stand slots; and
  a support bracket extending from the support stand, the support bracket comprising a plurality of bracket slots,
wherein the stand slots and the bracket slots are respectively dimensioned to secure each of said connectors to said support stand and said support bracket for connection to said respective one of said surgical instruments supported by said support stand to provide said fluid thereto, and
wherein said securing system comprises a plurality of polymeric restraints coupled to said support stand, each of said polymeric restraints being configured to force said respective one of said surgical instruments toward said support stand to secure said respective one of said surgical instruments to said support stand.

2. A rack as described in claim 1, wherein said filter defines said first and second fluid paths.

3. A rack as described in claim 1, wherein said filter comprises a housing having a removable filter cartridge disposed therein.

4. A rack as described in claim 1, wherein said filter is positioned between said fluid inlet and said first and second fluid paths.

5. A rack as described in claim 1, wherein said support bracket comprises a plurality of bracket positions, said bracket positions each being configured to secure one of said connectors for connection to said respective one of said surgical instruments to provide fluid thereto.

6. A rack as described in claim 1, wherein each of said connectors is one of a plurality of types of connectors, each of said connector types being configured to connect to a corresponding type of said surgical instruments to provide fluid thereto.

7. A rack as described in claim 6, wherein said stand slots are configured to mount one of said connector types on said support stand, and
  wherein said bracket slots are configured to mount another one of said connector types on said support stand.

8. A rack as described in claim 1, wherein each of said polymeric restraints comprises a body portion and a pair of end portions oppositely extending from the body,
  wherein each of the end portions of the polymeric restraints is configured to attach to said support stand.

9. A rack as described in claim 8, wherein a plurality of apertures are formed in said support stand,
  wherein each of said end portions of said polymeric restraints is positioned and secured within said apertures.

10. A rack as described in claim 9, wherein each of said body portions is configured to extend around said respective one of said surgical instruments to force said respective one of said surgical instruments toward said support stand.

11. A rack as described in claim 10, wherein each of said body portions is further configured to elastically extend around said respective one of said surgical instruments from said end portions of said polymeric restraints secured within said apertures.

* * * * *